US010687520B2

United States Patent
Min et al.

(10) Patent No.: US 10,687,520 B2
(45) Date of Patent: Jun. 23, 2020

(54) GENERATION AND CORRECTION OF A HUMANIZED MOUSE MODEL WITH A DELETION OF DYSTROPHIN EXON 44

(71) Applicant: The Board of Regents of the University of Texas System, Austin, TX (US)

(72) Inventors: Yi-Li Min, Dallas, TX (US); Rhonda Bassel-Duby, Dallas, TX (US); Eric Olson, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/914,728

(22) Filed: Mar. 7, 2018

(65) Prior Publication Data
US 2018/0271069 A1 Sep. 27, 2018

Related U.S. Application Data

(60) Provisional application No. 62/468,154, filed on Mar. 7, 2017.

(51) Int. Cl.

| | |
|---|---|
| *A01K 67/00* | (2006.01) |
| *C12N 15/00* | (2006.01) |
| *C07H 21/02* | (2006.01) |
| *C07H 21/04* | (2006.01) |
| *A01K 67/027* | (2006.01) |
| *C12N 9/22* | (2006.01) |
| *C12N 9/96* | (2006.01) |
| *C12N 15/11* | (2006.01) |
| *A61K 38/46* | (2006.01) |
| *A61K 31/7105* | (2006.01) |
| *A61P 21/00* | (2006.01) |
| *C12N 15/113* | (2010.01) |
| *A61K 48/00* | (2006.01) |
| *C12N 15/85* | (2006.01) |

(52) U.S. Cl.
CPC ...... *A01K 67/0276* (2013.01); *A61K 31/7105* (2013.01); *A61K 38/465* (2013.01); *A61P 21/00* (2018.01); *C12N 9/22* (2013.01); *C12N 9/96* (2013.01); *C12N 15/11* (2013.01); *C12N 15/113* (2013.01); *A01K 2207/12* (2013.01); *A01K 2207/15* (2013.01); *A01K 2217/054* (2013.01); *A01K 2217/056* (2013.01); *A01K 2217/075* (2013.01); *A01K 2227/105* (2013.01); *A01K 2267/0306* (2013.01); *A61K 48/005* (2013.01); *C07H 21/02* (2013.01); *C12N 15/8509* (2013.01); *C12N 2310/20* (2017.05); *C12N 2750/14143* (2013.01); *C12N 2800/80* (2013.01)

(58) Field of Classification Search
CPC .......... A01K 67/0276; A01K 2217/054; A01K 2217/056; C12N 15/8509; C07H 21/02; C07H 21/04
USPC .................................... 800/18, 21; 536/23.1
See application file for complete search history.

(56) References Cited

U.S. PATENT DOCUMENTS

| | | | |
|---|---|---|---|
| 2012/0301456 A1 | 11/2012 | Tremblay et al. | |
| 2014/0179770 A1 | 6/2014 | Zhang et al. | |
| 2015/0056705 A1 | 2/2015 | Conway et al. | |
| 2016/0090607 A1 | 3/2016 | Conway et al. | |
| 2016/0201089 A1 | 7/2016 | Gersbach et al. | |
| 2016/0208243 A1 | 7/2016 | Zhang et al. | |
| 2017/0362635 A1 | 12/2017 | Chamberlain et al. | |

FOREIGN PATENT DOCUMENTS

| | | |
|---|---|---|
| EP | 0273085 | 7/1988 |
| WO | WO 2016/025469 | 2/1916 |
| WO | WO 2016/089866 | 6/1916 |
| WO | WO 2016/115543 | 7/1916 |
| WO | WO 2016/174056 | 11/1916 |
| WO | WO 2017/095967 | 6/1917 |
| WO | WO 2014/197748 | 12/2014 |

OTHER PUBLICATIONS

Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*

(Continued)

*Primary Examiner* — Shin Lin Chen
(74) *Attorney, Agent, or Firm* — Parker Highlander PLLC

(57) ABSTRACT

Duchenne muscular dystrophy (DMD), which affects 1 in 5,000 male births, is one of the most common genetic disorders of children. This disease is caused by an absence or deficiency of dystrophin protein in striated muscle. The major DMD deletion "hot spots" are found between exon 6 to 8, and exons 45 to 53. Here, a "humanized" mouse model is provided that can be used to test a variety of DMD exon skipping strategies. Among these are, CRISPR/Cas9 oligo-nucleotides, small molecules or other therapeutic modalities that promote exon skipping or micro dystrophin mini genes or cell based therapies. Methods for restoring the reading frame of exon 44 deletion via CRISPR-mediated exon skipping in the humanized mouse model, in patient-derived iPS cells and ultimately, in patients using various delivery systems are also contemplated. The impact of CRISPR technology on DMD is that gene editing can permanently correct mutations.

6 Claims, 7 Drawing Sheets
Specification includes a Sequence Listing.

(56) References Cited

OTHER PUBLICATIONS

Maksmenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Aartsma-Rus et al., "Theoretic applicability of antisense-mediated exon skipping for Duchenne muscular dystrophy mutations," *Hum. Mutat.*, 30:293-299, 2009.
Aartsma-Rus, "Overview on DMD exon skipping," Methods Mol. Biol., 867:97-116, 2012.
Amoasii et al., "Single-cut genome editing restores dystrophin expression in a new mouse model of muscular dystrophy," *Sci. Transl. Med.*, 9(418):1-23, 2017.
Angel et al., "12-0-Tetradecanoyl-Phorbol-13-Acetate Induction of the Human Collagenase Gene is Mediated by an Inducible Enhancer Element Located in the 5'-Flanking Region," *Mol. Cell. Biol.*, 7:2256, 1987.
Angel et al., "Phorbol ester-inducible genes contain a common cis element recognized by a TPA-modulated trans-acting factor," *Cell*, 49:729, 1987.
Araki et al., "Targeted Disruption of Exon 52 in the Moue Dystrophin Gene Induced Muscle Degeneration Similar to That Observed in Duchenne Muscular Dystrophy.," *Biochem. Biophys. Res. Comm.*, 238:492-497, 1997.
Baichwal and Sugden, In: Gene Transfer, Kucherlapati (Ed), NY, Plenum Press, pp. 117-148, 1986.
Banerji et al., "A lymphocyte-specific cellular enhancer is located downstream of the joining region in immunoglobulin heavy chain genes," *Cell*, 33(3):729-740, 1983.
Banerji et al., "Expression of a β-globin gene is enhanced by remote SV40 DNA sequences," *Cell*, 27(2 Pt 1):299-308, 1981.
Barnes et al., "Cloning of cardiac, kidney, and brain promoters of the feline ncx1 gene," *J. Biol. Chem.*, 272(17):11510-11517, 1997.
Baskin et al., "MED13-dependent signaling from the heart confers leanness by enhancing metabolism in adipose tissue and liver," EMBO Mol. Med., 6:1610-1621, 2014.
Bengtsson et al: "Progress and prospects of gene therapy clinical trials for the muscular dystrophies," Human Molecular Genetics, 25(R1):R9-R17, 2016.
Benvenisty and Neshif, "Direct introduction of genes into rats and expression of the genes," *Proc. Natl. Acad. Sci. USA*, 83:9551-9555, 1986.
Berkhout et al., "Tat trans—activates the human immunodeficiency virus through a nascent RNA target," *Cell*, 59:273-282, 1989.
Bhavsar et al., "Isolation and characterization of the human cardiac troponin I gene (TNNI3)," *Genomics*, 35(1):11-23, 1996.
Bikard et al., "Programmable repression and activation of bacterial gene expression using an engineered CRISPR-Cas System," *Nucleic Acids Res.* 41(15):7429-7437, 2013.
Blanar et al., "A gamma-interferon-induced factor that binds the interferon response sequence of the MHC class I gene, H-2Kb," *EMBO J.*, 8:1139, 1989.
Bodine and Ley, "An enhancer element lies 3' to the human A gamma globin gene," *EMBO J.*, 6:2997, 1987.
Boshart et al., "A very strong enhancer is located upstream of an immediate early gene of human cytomegalovirus," *Cell*, 41:521, 1985.
Bostick et al., "AAV-microdystrophin therapy improves cardiac performance in aged female mdx mice," *Mol. Ther.*, 19:1826-1832, 2011.
Bosze et al., "A transcriptional enhancer with specificity for erythroid cells is located in the long terminal repeat of the Friend murine leukemia virus," *EMBO J.*, 5(7):1615-1623, 1986.
Braddock et al., "HIV-1 TAT "activates" presynthesized RNA in the nucleus," *Cell*, 58:269, 1989.
Brinster et al., "Factors affecting the efficiency of introducing foreign DNA into mice by microinjecting eggs," *Proc. Natl. Acad. Sci. USA*, 82(13):4438-4442, 1985.
Bulla and Siddiqui, "The hepatitis B virus enhancer modulates transcription of the hepatitis B virus surface antigen gene from an internal location," *J. Virol.*, 62(4):1437-1441, 1988.
Burridge et al., "Chemically defined generation of human cardiomyocytes," *Nat. Methods*, 11(8):855-860, 2014.
Bushby et al., "Diagnosis and management of Duchenne muscular dystrophy, part 1: diagnosis, and pharmacological and psychosocial management," *Lancet Neurol.*, 9(1):7793, 2010.
Bushby et al., "Diagnosis and management of Duchenne muscular dystrophy, part 2: implementation of multidisciplinary care," *Lancet Neurol.*, 9(2):177-189, 2010.
Campbell and Kahl, "Association of dystrophin and an integral membrane glycoprotein," *Nature*, 338:259-262, 1989.
Campbell and Villarreal, "Functional analysis of the individual enhancer core sequences of polyomavirus: cell-specific uncoupling of DNA replication from transcription," *Mol. Cell. Biol.*, 8(5):1993-2004, 1988.
Campere and Tilghman, "Postnatal repression of the alpha-fetoprotein gene is enhancer independent," *Genes Dev.*, 3:537-546, 1989.
Campo et al., "Transcriptional control signals in the genome of bovine papillomavirus type 1," *Nature*, 303:77, 1983.
Celander and Haseltine, "Glucocorticoid regulation of murine leukemia virus transcription elements is specified by determinants within the viral enhancer region," *J. Virol.*, 61(2):269-275, 1987.
Celander et al., "Regulatory elements within the murine leukemia virus enhancer regions mediate glucocorticoid responsiveness," *J. Virol.*, 62(4):1314-1322, 1988.
Chandler et al., "DNA sequences bound specifically by glucocorticoid receptor in vitro render a heterologous promoter hormone responsive in vivo," *Cell*, 33:489, 1983.
Chang et al., "Glucose-regulated protein (GRP94 and GRP78) genes share common regulatory domains and are coordinately regulated by common trans-acting factors," *Mol. Cell. Biol.*, 9:2153, 1989.
Chang et al., "Polycistronic lentiviral vector for "hit and run" reprogramming of adult skin fibroblasts to induced pluripotent stem cells," *Stem Cells*, 27:1042-1049, 2009.
Chatterjee et al., "Negative regulation of the thyroid-stimulating hormone alpha gene by thyroid hormone: receptor interaction adjacent to the TATA box," *Proc. Natl. Acad. Sci. USA*, 86:9114-9118, 1989.
Chen and Okayama, "High-efficiency transformation of mammalian cells by plasmid DNA," *Mol. Cell Biol.*, 7:2745-2752, 1987.
Cho et al., "Targeted genome engineering in human cells with the Cas9 RNA-guided endonuclease," *Nat. Biotechnol.* 31(3):230-232, 2013.
Choi et al., "An altered pattern of cross-resistance in multidrug-resistant human cells results from spontaneous mutations in the mdr1 (P-glycoprotein) gene," *Cell*, 53:519, 1988.
Cirak et al., "Exon skipping and dystrophin restoration in patients with Duchenne muscular dystrophy after systemic phosphorodiamidate morpholino oligomer treatment: an open-label, phase 2, dose-escalation study," *Lancet*, 378(9791):595-605, 2011.
Coffin, In: Virology, Fields et al. (Eds.), Raven Press, NY, pp. 1437-1500, 1990.
Cohen et al., "A repetitive sequence element 3' of the human c-Ha-ras1 gene has enhancer activity," *J. Cell. Physiol.*, 5:75, 1987.
Cong et al., "Multiplex genome engineering using CRISPR/Cas systems," *Science*, 339:819-823, 2013.
Costa et al., "The cell-specific enhancer of the mouse transthyretin (prealbumin) gene binds a common factor at one site and a liver-specific factor (s) at two other sites," *Mol. Cell. Biol.*, 8:81, 1988.
Couch et al "Immunization with types 4 and 7 adenovirus by selective infection of the intestinal tract," *Am. Rev. Resp. Dis.*, 88:394-403, 1963.
Coupar et al., "A general method for the construction of recombinant vaccinia viruses expressing multiple foreign genes," *Gene*, 68:1-10, 1988.
Cripe et al., "Transcriptional regulation of the human papillomavirus-16 E6-E7 promoter by a keratinocyte-dependent enhancer, and by viral E2 trans-activator and repressor gene products: implications for cervical carcinogenesis," *EMBO J.*, 6:3745-3753, 1987.

(56) References Cited

OTHER PUBLICATIONS

Culotta and Hamer, "Fine mapping of a mouse metallothionein gene metal response element," *Mol. Cell. Biol.*, 9:1376, 1989.
Dandolo et al., "Regulation of polyoma virus transcription in murine embryonal carcinoma cells," *J. Virol.*, 47:55-64, 1983.
De Villiers et al., "Polyoma virus DNA replication requires an enhancer," *Nature*, 312(5991):242-246, 1984.
Deans et al., "A tunable genetic switch based on RNAi and repressor proteins for regulating gene expression in mammalian cells," *Cell*, 130:363-372, 2007.
Deschamps et al., "Identification of a transcriptional enhancer element upstream from the proto-oncogene fos," *Science*, 230:1174-1177, 1985.
DeWitt et al., "Selection-free genome editing of the sickle mutation in human adult hematopoietic stem/progenitor cells," *Sci. Transl. Med.*, 8 (360):360ra134, 2016.
Donnelly et al., "The 'cleavage' activities of foot-and-mouth disease virus 2A site-directed mutants and naturally occurring '2A-like'sequences," *J. Gen. Virol.* 82, 1027-1041, 2001.
Duan et al., "Genome-wide identification of CRISPR/Cas9 off-targets in human genome," *Cell Res.*, 24:1009-1012, 2014.
Dubensky et al., "Direct transfection of viral and plasmid DNA into the liver or spleen of mice," *Proc. Natl. Acad. Sci. USA*, 81:7529-7533, 1984.
Echigoya et al, "Dystrophin Exon 52-Deleted Pigs as a New Animal Model of Duchenne Muscular Dystrophy: its Caracterization and Potenial as a Tool for Developing Exon Skipping Therapy," *Mol. Ther.*, 24(Suppl. 1): S247, Abstract 623, 2016.
Edbrooke et al., "Identification of cis-Acting Sequences Responsible for Phorbol Ester Induction of Human Serum Amyloid A Gene Expression via a Nuclear Factor KB-Like Transcription Factor," *Mol. Cell. Biol.*, 9:1908, 1989.
Edlund et al., "Cell-specific expression of the rat insulin gene: evidence for role of two distinct 5'flanking elements," *Science*, 230:912-916, 1985.
Fairclough et al., "Therapy for Duchenne muscular dystrophy: renewed optimism from genetic approaches," *Nat. Rev. Genet.*, 14:373-378, 2013.
Fechheimer et al., "Transfection of mammalian cells with plasmid DNA by scrape loading and sonication loading," *Proc Natl. Acad. Sci. USA*, 84:8463-8467, 1987.
Feng and Holland, "HIV-1 tat trans-activation requires the loop sequence within tar," *Nature*, 334(6178):165-167, 1988.
Ferkol et al., "Regulation of the phosphoenolpyruvate carboxykinase/humanfactor IX gene introduced into the livers of adult rats by receptor-mediated gene transfer," *FASEB J.*, 7:1081-1091, 1993.
Firak and Subramanian, "Minimal transcriptional enhancer of simian virus 40 is a 74-base-pair sequence that has interacting domains," *Mol. Cell. Biol.*, 6(11):3667-3676, 1986.
Flanigan et al., "Mutational spectrum of DMD mutations in dystrophinopathy patients: application of modern diagnostic techniques to a large cohort ," *Hum. Mutat.*, 30(12):1657-1666, 2009.
Foecking and Hofstetter, "Powerful and versatile enhancer-promoter unit for mammalian expression vectors," *Gene*, 45(1):101-105, 1986.
Fonfara et al., "The CRISPR-associated DNA-cleaving enzyme Cpf1 also processes precursor CRISPR RNA," *Nature*, 532:517-521, 2016.
Fraley et al., "Entrapment of a bacterial plasmid in phospholipid vesicles: potential for gene transfer," *Proc Natl. Acad. Sci. USA*, 76:3348-3352, 1979.
Franz et al., "Characterization of a cardiac-selective and developmentally upregulated promoter in transgenic mice," *Cardioscience*, 5(4):235-43, 1994.
Friedmann, "Progress toward human gene therapy," *Science*, 244:1275-1281, 1989.
Fu et al., "High-frequency off-target mutagenesis induced by CRISPR-Cas nucleases in human cells," *Nat. Biotechnol.*, 31:822-826, 2013.

Fujita et al., "Interferon-β gene regulation: tandemly repeated sequences of a synthetic 6 bp oligomer function as a virus-inducible enhancer," *Cell*, 49:357, 1987.
Ghosh and Bachhawat, In: Liver Diseases, Targeted Diagnosis and Therapy Using Specific Receptors and Ligands, Wu et al. (Eds.), Marcel Dekker, NY, pp. 87-104, 1991.
Ghosh-Choudhury et al., "Protein IX, a minor component of the human adenovirus capsid, is essential for the packaging of full length genomes," *EMBO J.*, 6:1733-1739, 1987..
Gibson et al., "Enzymatic assembly of DNA molecules up to several hundred kilobases," *Nature Methods*, 6:343-345, 2009.
Gilles et al., "A tissue-specific transcription enhancer element is located in the major intron of a rearranged immunoglobulin heavy chain gene," *Cell*, 33:717-728, 1983.
Gjerdrum et al., "Laser-Assisted Microdissection of Membrane-Mounted Paraffin Sections for Polymerase Chain Reaction Analysis," *J. Mol. Diagn.*, 3(3):105-110, 2001.
Gloss et al., "The upstream regulatory region of the human papilloma virus-16 contains an E2 protein-independent enhancer which is specific for cervical carcinoma cells and regulated by glucocorticoid hormones," *EMBO J.*, 6:3735, 1987.
Gomez-Foix et al., "Adenovirus-mediated transfer of the muscle glycogen phosphorylase gene into hepatocytes confers altered regulation of glycogen metabolism," *J. Biol. Chem.*, 267:25129-25134, 1992.
Goncalves et al., "Transcription factor rational design improves directed differentiation of human mesenchymal stem cells into skeletal myocytes," *Mol. Ther.*, 19(7): 1331-1341, 2011.
Goodbourn and Maniatis, "Overlapping positive and negative regulatory domains of the human beta-interferon gene," *Proc. Natl. Acad. Sci. USA*, 85:1447, 1988.
Goodbourn et al., "The human β-interferon gene enhancer is under negative control," *Cell*,45:601, 1986.
Gopal, "Gene transfer method for transient gene expression, stable transformation, and cotransformation of suspension cell cultures," *Mol. Cell Biol.*, 5:1188-1190, 1985.
Gopal-Srivastava et al., "Regulation of the murine alpha B-crystallin/small heat shock protein gene in cardiac muscle," *J. Mol. Cell. Biol.*, 15(12):7081-7090, 1995.
Graham and Prevec, "Manipulation of adenovirus vectors," In: Methods in Molecular Biology: Gene Transfer and Expression Protocol, Murray (Ed.), Humana Press, Clifton, NJ, 7:109-128, 1991.
Graham and van der Eb, "A new technique for the assay of infectivity of human adenovirus 5 DNA," *Virology*, 52:456-467, 1973.
Graham et al., "Characteristics of a human cell line transformed by DNA from human adenovirus type 5," *J. Gen. Virol.*, 36:59-72, 1977.
Greene et al., "HIV-1, HTLV-1, and normal T cell growth: transcriptional strategies and surprises," *Immunol. Today*, 10:272, 1989.
Grosschedl and Whitehead, "Cell-type specificity of immunoglobulin gene expression is regulated by at least three DNA sequence elements," *Cell*, 41:885, 1985.
Grunhaus and Horwitz, "Adenoviruses as cloning vectors," *Semin. Virol.*, 3:237-252, 1992.
Harland and Weintraub, "Translation of mRNA injected into Xenopus oocytes is specifically inhibited by antisense RNA.," *J. Cell Biol.*, 101:1094-1099, 1985.
Harris et al., "Tissue-specific gene delivery via nanoparticle coating,"*Biomaterials*, 31:998-1006, 2010.
Haslinger and Karin, "Upstream promoter element of the human metallothionein-IIA gene can act like an enhancer element," *Proc. Natl. Acad. Sci. USA*, 82:8572, 1985.
Hauber and Cullen, "Mutational analysis of the trans-activation-responsive region of the human immunodeficiency virus type I long terminal repeat," *J. Virol.*, 62:673, 1988.
Hen et al., "A mutated polyoma virus enhancer which is active in undifferentiated embryonal carcinoma cells is not repressed by adenovirus-2 ELA products," *Nature*, 321:249-251, 1986.
Hensel et al., "PMA-responsive 5'flanking sequences of the human TNF gene," *Lymphokine Res.*, 8:347, 1989.

(56) References Cited

OTHER PUBLICATIONS

Hermonat and Muzycska, "Use of adeno-associated virus as a mammalian DNA cloning vector: transduction of neomycin resistance into mammalian tissue culture cells," *Natl. Acad. Sci. USA*, 81:6466-6470, 1984.
Herr and Clarke, "The SV40 enhancer is composed of multiple functional elements that can compensate for one another," *Cell*, 45:461, 1986.
Herz and Gerard, "Adenovirus-mediated transfer of low density lipoprotein receptor gene acutely accelerates cholesterol clearance in normal mice," *Proc. Natl. Acad. Sci. USA*, 90:2812-2816, 1993.
Hesdorffer et al., "Efficient Gene Transfer in Live Mice Using a Unique Retroviral Packaging Line," *DNA Cell Biol.*, 9:713-723, 1990.
Hirochika et al., "Enhancers and trans-acting E2 transcriptional factors of papillomaviruses," *J. Virol.*, 61:2599, 1987.
Holbrook et al., "Cis-acting transcriptional regulatory sequences in the gibbon ape leukemia virus (GALV) long terminal repeat," *Virology*, 157:211, 1987.
Hollinger and Chamberlain, "Viral vector mediated gene therapies," *Curr. Opin. Neurol.*, 28, 522-527, 2015.
Horlick and Benfield, "The upstream muscle-specific enhancer of the rat muscle creatine kinase gene is composed of multiple elements," *Mol. Cell. Biol.*, 9:2396, 1989.
Horwich et al., "Synthesis of hepadnavirus particles that contain replication-defective duck hepatitis B virus genomes in cultured HuH7 cells," *J. Virol.*, 64:642-650, 1990.
Hsu et al., "Development and applications of CRISPR-Cas9 for genome engineering," *Cell*, 157:1262-1278, 2014.
Hsu et al., "DNA targeting specificity of RNA-guided Cas9 nucleases," *Nat. Biotechnol.*, 31:827-832, 2013.
Huang et al., Glucocorticoid regulation of the Ha-MuSV p21 gene conferred by sequences from mouse mammary tumor virus, *Cell*, 27:245, 1981.
Hug et al., "Organization of the murine Mx gene and characterization of its interferon- and virus-inducible promoter," Mol. Cell. Biol., 8:3065, 1988.
Hwang et al., "Characterization of the S-Phase-Specific Transcription Regulatory Elements in a DNA Replication-Independent Testis-Specific H2B (TH2B) Histone Gene," *Mol. Cell. Biol.*, 10:585, 1990.
Imagawa et al., "Transcription factor AP-2 mediates induction by two different signal-transduction pathways: Protein kinase C and Camp," *Cell*, 51:251-260, 1987.
Imbra and Karin, "Phorbol ester induces the transcriptional stimulatory activity of the SV40 enhancer," *Nature*, 323:555, 1986.
Imler et al., "Negative Regulation Contributes to Tissue Specificity of the Immunoglobulin Heavy-Chain Enhancer," *Mol. Cell. Biol.*, 7:2558-2567, 1987.
Imperiale and Nevins, "Adenovirus 5 E2 transcription unit: an E1A-inducible promoter with an essential element that functions independently of position or orientation," *Mol. Cell. Biol.*, 4:875-882, 1984.
Iyombe-Engembe et al., "Efficient restoration of the dystrophin gene reading frame and protein structure in DMD myoblasts using the cindel method," *Mol. Ther. Nucleic Acids*, 5:e283, 2016.
Jakobovits et al., "A discrete element 3' of human immunodeficiency virus 1 (HIV-1) and HIV-2 mRNA initiation sites mediates transcriptional activation by an HIV trans activator," *Mol. Cell. Biol.*, 8:2555, 1988.
Jameel and Siddiqui, "The human hepatitis B virus enhancer requires trans-acting cellular factor(s) for activity," *Mol. Cell. Biol.*, 6:710-715, 1986.
Jaynes et al., "The muscle creatine kinase gene is regulated by multiple upstream elements, including a muscle-specific enhancer," *Mol. Cell. Biol.*, 8:62-70, 1988.
Jinek et al., "A programmable dual-RNA-guided DNA endonuclease in adaptive bacterial imunity," *Science*, 337:816-821, 2012.
Johnson et al., "Muscle creatine kinase sequence elements regulating skeletal and cardiac muscle expression in transgenic mice," *Mol. Cell. Biol.*, 9:3393, 1989.
Jones and Shenk, "Isolation of deletion and substitution mutants of adenovirus type 5," *Cell*, 13:181-188, 1978.
Kadesch and Berg, "Effects of the position of the simian virus 40 enhancer on expression of multiple transcription units in a single plasmid," *Mol. Cell. Biol.*, 6:259-26013, 1986.
Kaneda et al., "Increased expression of DNA cointroduced with nuclear protein in adult rat liver," *Science*, 243:375-378, 1989.
Karin et al., "Metal-responsive elements act as positive modulators of human metallothionein-IIA enhancer activity," *Mol. Cell. Biol.*, 7:606-613, 1987.
Karlsson et al., "Stable gene transfer and tissue-specific expression of a human globin gene using adenoviral vectors," *EMBO J*, 5:2377-2385, 1986.
Katinka et al., "Expression of polyoma early functions in mouse embryonal carcinoma cellsdepends on sequence rearrangements in the beginning of the late region," *Cell*, 20:393-399, 1980.
Kato et al., "Expression of Hepatitis B Virus Surface Antigen in Adult Rat Liver," *J. Biol Chem.*, 266(6):3361-3364, 1991.
Kawamoto et al., "Identification of the human beta-actin enhancer and its binding factor," *Mol. Cell. Biol.*, 8:267, 1988.
Kelly et al., "Myosin light chain 3F regulatory sequences confer regionalized cardiac and skeletal muscle expression in transgenic mice," *J. Cell Biol.*, 129(2):383-96,1995.
Kiledjian et al., "Identification and characterization of two functional domains within the murine heavy-chain enhancer," *Mol. Cell. Biol.*, 8:145, 1988.
Kim et al., "Genome-wide analysis reveals specificities of Cpf1 endonucleases in human cells," *Nat. Biotechnol.*, 34, 863-868, 2016.
Kimura et al., "A 900 bp genomic region from the mouse dystrophin promoter directs lacZ reporter expression only to the right heart of transgenic mice," *Dev. Growth Differ.*, 39(3):257-65, 1997.
Klamut et al., "Molecular and Functional Analysis of the Muscle-Specific Promoter Region of the Duchenne Muscular Dystrophy Gene," *Mol. Cell. Biol.*, 10:193-205, 1990.
Klein et al., "High-velocity microprojectiles for delivering nucleic acids into living cells," *Nature*, 327:70-73, 1987.
Kleinstiver et al., "Genome-wide specificities of CRISPR-Cas Cpf1 nucleases in human cells," *Nature Biotechnolog*, 34:869-874, 2016.
Koch et al., "Anatomy of a New B-Cell-Specific Enhancer," *Mol. Cell. Biol.*, 9:303, 1989.
Kodippili et al., "Characterization of 65 Epitope-Specific Dystrophin Monoclonal Antibodies in Canine and Murine Models of Duchenne Muscular Dystrophy by Immunostaining and Western Blot," *PLoS One*, 9:e88280, 2014.
Kormann et al., "Expression of therapeutic proteins after delivery of chemically modified mRNA in mice," *Nat Biotechnol* 29, 154-157, 2011.
Kriegler and Botchan, "Enhanced Transformation by a Simian Virus 40 Recombinant Virus Containing a Harvey Murine Sarcoma Virus Long Repeat," *Mol. Cell. Biol.*,3:325-339, 1983.
Kriegler et al., "A novel form of TNF/cachectin is a cell surface cytotoxic transmembrane protein: Ramifications for the complex physiology of TNF," *Cell*, 53:45-53, 1988.
Kriegler et al., "Transformation mediated by the SV40 T antigens: Separation of the overlapping SV40 early genes with a retroviral vector," *Cell*, 38:483-491, 1984.
Kuhl et al., "Reversible silencing of enhancers by sequences derived from the human IFN-α promoter," *Cell*, 50:1057, 1987.
Kunz et al., "Identification of the promoter sequences involved in the interleukin-6 dependent expression of the rat α2-macroglobulin gene," *Nucl. Acids Res.*, 17:1121-1138, 1989.
Kuscu et al., "Genome-wide analysis reveals characteristics of off-target sites bound by the Cas9 endonuclease," *Nat Biotechnol* 32, 677-683, 2014.
La Salle et al., "An adenovirus vector for gene transfer into neurons and glia in the brain," Science, 259:988-990, 1993.
LaPointe et al., "Tissue-specific expression of the human brain natriuretic peptide gene in cardiac myocytes," *Hypertension*, 27(3):715-22, 1996.

(56) References Cited

OTHER PUBLICATIONS

LaPointe et al., "Upstream Sequences Confer Atrial-specific Expression on the Human Atrial Natriuretic Factor Gene," *J. Biol. Chem.*, 263(19):9075-8, 1988.

Larsen et al., "Repression mediates cell-type-specific expression of the rat growth hormone gene," *Proc. Natl. Acad. Sci. USA.*, 83:8283-8287, 1986.

Laspia et al., "HIV-1 Tat protein increases transcriptional initiation and stabilizes elongation," *Cell*, 59:283-282, 1989.

Latimer et al., "Highly Conserved Upstream Regions of the oLI-Antitrypsin Gene in Two Mouse Species Govern Liver-Specific Expression by Different Mechanisms," *Mol. Cell. Biol.*, 10:760-769, 1990.

Lee et al., "Glucocorticoids regulate expression of dihydrofolate reductase cDNA in mouse mammary tumour virus chimaeric plasmids," *Nature*, 294:228, 1981.

Levinson et al., "Activation of SV40 genome by 72-base pair tandem repeats of Moloney sarcoma virus," *Nature*, 295:79, 1982.

Levrero et al., "Defective and nondefective adenovirus vectors for expressing foreign genes in vitro and in vivo," *Gene*, 101:195-202, 1991.

Li et al., "Engineered Nuclease Mediated Genetic Correction in iPSCs Derived From Duchenne Muscular Dystrophy Patient," *Mol. Ther.*, 22(Supp. 1):5124 (Abstract 322), 2014.

Li et al., "Generation of Destabilized Green Fluorescent Protein as a Transcription Reporter," *J. Biol. Chem.*, 273:34970-34975, 1998.

Li et al., "Precise correction of the dystrophin gene in duchenne muscular dystrophy patient induced pluripotent stem cells by TALEN and CRISPR-Cas9," *Stem Cell Reports*, 4(1):143154, 2015.

Lin et al., "Delineation of an enhancerlike positive regulatory element in the interleukin-2 receptor alpha-chain gene," *Mol. Cell. Biol.*, 10:850, 1990.

Long et al., "Postnatal genome editing partially restores dystrophin expression in a mouse model of muscular dystrophy," *Science*, 351(6271):400-403, 2015.

Long et al., "Prevention of muscular dystrophy in mice by CRISPR/Cas9-mediated editing of germline DNA," *Science*, 345(6201):1184-1188, 2014.

Long et al., Genome Editing of Monogenic Neuromuscular Diseases: A Systematic Review, *JAMA Neurol.*, 73 (11) : 1349-1355, 2016.

Luria et al., "Promoter and enhancer elements in the rearranged a chain gene of the human T cell receptor," *EMBO J.*, 6:3307-3312, 1987.

Lusky and Botchan, "Transient replication of bovine papilloma virus type 1 plasmids: cis and trans requirements,":*Proc. Natl. Acad. Sci. USA*, 83:3609, 1986.

Lusky et al., "Bovine papilloma virus contains an activator of gene expression at the distal end of the early transcription unit," *Mol. Cell. Biol.*, 3:1108-1122, 1983.

Maggio et al., "Selection-free gene repair after adenoviral vector transduction of designer nucleases: rescue of dystrophin synthesis in DMD muscle cell populations," *Nucleic Acids Res.*, 44(3):1449-1470, 2016.

Majors and Varmus, "A small region of the mouse mammary tumor virus long terminal repeat confers glucocorticoid hormone on a linked heterologous gene," *Proc. Natl. Acad. Sci. USA*, 80:5866-5870, 1983.

Mali et al., "Cas9 as a versatile tool for engineering biology," Nat Methods 10, 957-963, 2013.

Mali et al., "CAS9 transcriptional activators for target specificity screening and paired nickases for cooperative genome engineering," *Nat. Biotechnol.* 31:833-838, 2013.

Mali et al., "RNA-guided human genome engineering via Cas9," *Science*, 339:823-826, 2013.

Mann et al., "Antisense-induced exon skipping and synthesis of dystrophin in the Mdx mouse," *PNAS*, vol. 98, No. 1, pp. 42-47, 2001.

Mann et al., "Construction of a retrovirus packaging mutant and its use to produce helper-free defective retrovirus," *Cell*, 33:153-159, 1983.

Maresca et al., "Obligate Ligation-Gated Recombination (ObLiGaRe): Custom-designed nuclease-mediated targeted integration through nonhomologous end joining," *Genome Research* 23, 539-546, 2013.

Markowitz et al., "A Safe Packaging Line for Gene Transfer: Separating Viral Genes on Two Different Plasmids," *J. Virol.*, 62:1120-1124, 1988.

Martari, M., et al. "Partial Rescue of Growth Failure in Growth Hormone (GH)-Deficient Mice by a Single Injection of a Double-Stranded Adeno-Associated Viral Vector Expressing the GH Gene Driven by a Muscle-Specific Regulatory Cassette," *Hum Gene Ther*, 20(7):759-766 (2009).

McGreevy et al., "Animal models of Duchenne muscular dystrophy: from basic mechanisms to gene therapy," *Dis. Models Mech.*, 8:195-213, 2015.

McNeall et al., "Hyperinducible gene expression from a metallothionein promoter containing additional metal-responsive elements," *Gene*, 76:81, 1989.

Miksicek et al., "Glucocorticoid responsiveness of the transcriptional enhancer of Moloney Murine Sarcoma Virus," *Cell*, 46:203, 1986.

Millay et al., "Genetic and pharmacologic inhibition of mitochondrial-dependent necrosis attenuates muscular dystrophy," *Nat. Med.*, 14, 442-447, 2008.

Mojica et al., "Intervening Sequences of Regularly Spaced Prokaryotic Repeats Derive from Foreign Genetic Elements," *J. Mol. Evol.* 60, 174-182, 2005.

Montarras et al., "Direct Isolation of Satellite Cells for Skeletal Muscle Regeneration," *Science*, 309, 2064-2067, 2005.

Mordacq and Linzer, "Co-localization of elements required for phorbol ester stimulation and glucocorticoid repression of proliferin gene expression," *Genes and Dev.*, 3:760-769, 1989.

Moreau et al., "The SV40 72 base repair repeat has a striking effect on gene expression both in SV40 and other chimeric recombinants," *Nucl. Acids Res.*, 9:6047-6068, 1981.

Moss et al., "Hypothesis for a Serine Proteinase-like Domain at the COOH Terminus of Slowpoke Calcium-activated Potassium Channels," *J. Gen. Physiol.*, 108(6):473-84, 1996.

Mourkioti et al., "Role of telomere dysfunction in cardiac failure in Duchenne muscular dystrophy," *Nature Cell Biology* 15, 895-904, 2013.

Muesing et al., "Regulation of mRNA accumulation by a human immunodeficiency virus trans-activator protein," *Cell*, 48:691-701, 1987.

Murphy et al., "Satellite cells, connective tissue fibroblasts and their interactions are crucial for muscle regeneration," *Development* 138, 3625-3637, 2011.

Nakamura et al. "Generation of muscular dystrophy model rats with a CRISPR/Cas system," *Sci. Rep.*, 4(5635):1-6, 2014.

Nathwani et al., "Long-term safety and efficacy following systemic administration of a self-complementary AAV vector encoding human FIX pseudotyped with serotype 5 and 8 capsid proteins," *Molecular Therapy*, 19(5):876-885, 2011.

Nelson et al., "In vivo genome editing improves muscle function in a mouse model of Duchenne muscular dystrophy," *Science*, 351:403-407, 2016.

Nicholson et al., "Dystrophin in skeletal muscle II. Immunoreactivity in patients with Xp21 muscular dystrophy," *J Neuro Sci* 94, 137-146, 1989.

Nicolas and Rubinstein, In: Vectors: a survey of molecular cloning vectors and their uses, Rodriguez and Denhardt (Eds.), Stoneham: Butterworth, pp. 493-513, 1988.

Nicolau and Sene, "Liposome-mediated DNA transfer in eukaryotic cells: Dependence of the transfer efficiency upon the type of liposomes used and the host cell cycle stage," *Biochim. Biophys. Act*, 721:185-190, 1982.

Nicolau et al., "[16] Liposomes as carriers for in vivo gene transfer and expression," *Methods Enzymol.*, 149:157-176, 1987.

Ondek et al., "Discrete elements within the SV40 enhancer region display different cell-specific enhancer activities," *EMBO J.*, 6:1017, 1987.

(56) References Cited

OTHER PUBLICATIONS

Ornitz et al., "Promoter and Enhancer Elements from the Rat Elastase I Gene Function Independently of Each Other and of Heterologous Enhancers," *Mol. Cell. Biol.*, 7:3466, 1987.
Osborn et al., "Talen-based Gene Correction for Epidermolysis Bullosa," *Mol Ther* 21, 1151-1159, 2013.
Ousterout et al., "Genetic correction of Duchenne muscular dystrophy by multiplex CRISPR/Cas9-based gene editing," Abstract 509, Annual Meeting of American Society of Gene Therapy, May 2014.
Ousterout et al., "Multiplex CRISPR/Cas9-based genome editing for correction of dystrophin mutations that cause Duchenne muscular dystrophy," *Nat. Commun.*, 6:6244, 2015.
Ousterout et al., "Reading frame correction by targeted genome editing restores dystrophin expression in cells from Duchenne muscular dystrophy patients," *Mol Ther*, 21:1718-1726, 2013.
Padgett, "New connections between splicing and human disease," *Trends Genet.* 28, 147-154, 2012.
Palmiter et al., "Differential regulation of metallothionein-thymidine kinase fusion genes in transgenic mice and their offspring," *Cell*, 29:701, 1982.
Palmiter et al., "Dramatic growth of mice that develop from eggs microinjected with metallothionein—growth hormone fusion genes," *Nature*, 300:611, 1982.
Paskind et al., "Dependence of Moloney murine leukemia virus production on cell growth," *Virology*, 67:242-248, 1975.
Pattanayak et al., "High-throughput profiling of off-target DNA cleavage reveals RNA-programmed Cas9 nuclease specificity," *Nat Biotechnol* 31, 839-843, 2013.
PCT International Search Report and Written Opinion issued in International Application No. PCT/US2015/044639, dated Dec. 8, 2015.
Pech et al., "Functional Identification of Regulatory Elements within the Promoter Region of Platelet-Derived Growth Factor 2," *Mol. Cell. Biol.*, 9:396-405, 1989.
Peng et al., "In vivo plasmid DNA electroporation resulted in transfection of satellite cells and lasting transgene expression in regenerated muscle fibers," *Biochem Biophys Res Commun* 338, 1490-1498, 2005.
Perales et al., "Gene transfer in vivo: Sustained expression and regulation of genes introduced into the liver by receptor-targeted uptake," *Proc. Natl. Acad. Sci. USA*, 91(9):4086-4090, 1994.
Perez-Stable and Constantini, "Roles of Fetal G-γGlobin Promoter Elements and the Adult 3-Globin 3' Enhancer in the Stage-Specific Expression of Globin Genes," *Mol. Cell. Biol.*, 10:1116-1125, 1990.
Picard and Schaffner, "A lymphocyte-specific enhancer in the mouse immunoglobulin κ gene," *Nature*, 307:80-82, 1984.
Pigozzo et al., "Revertant Fibers in the mdx Murine Model of Duchenne Muscular Dystrophy: an Age- and Muscle-Related Reappraisal," *PLoS One* 8(8): e72147, 2013.
Pinello et al., "Analyzing CRISPR genome-editing experiments with CRISPResso," *Nature Biotechnol.* 34, 695-697, 2016.
Pinkert et al., "An Albumin Enhancer Located 10 kb Upstream Functions Along With Its Promoter to Direct Efficient, Liver-Specific Expression in Transfenic Mice," *Genes and Dev.*, 1 :268, 1987.
Ponta et al., "Hormonal response region in the mouse mammary tumor virus long terminal repeat can be dissociated from the proviral promoter and has enhanced properties," *Natl. Acad. Sci. USA*, 82:1020-1024, 1985.
Porton et al., "Immunoglobulin Heavy-Chain Enhancer Is Required to Maintain Transfected γ2A Gene Expression in a Pre-B-Cell Line," *Mol. Cell. Biol.*, 10:1076, 1990.
Potter et al., "Enhancer-dependent expression of human Κc immunoglobulin genes introduced into mouse pre-B lymphocytes by electroporation," *Proc. Natl. Acad. Sci. USA*, 81:7161-7165, 1984.
Queen and Baltimore, "Immunoglobulin gene transcription is activated by downstream sequence elements," *Cell*, 35:741, 1983.
Quinn et al., "Multiple Components Are Required for Sequence Recognition of the AP1 . Site in the Gibbon Ape Leukemia Virus Enhancer," *Mol. Cell. Biol.*, 9:4713-4721, 1989.

Racher et al., "Culture of 293 cells in different culture systems: Cell growth and recombinant adenovirus production," Biotech Techniques, 9:169-174, 1995.
Ragot et al., "Efficient adenovirus-mediated transfer of a human minidystrophin gene to skeletal muscle of mdx mice," *Nature*, 361:647-650, 1993.
Ran et al., "In vivo genome editing using *Staphylococcus aureus* Cas9," *Nature* 520, 186-191, 2015.
Redondo et al., "A T cell-specific transcriptional enhancer within the human T cell receptor delta locus," *Science*, 247:1225, 1990.
Reisman and Rotter, "Induced Expression from the Moloney Murine Leukemia Virus Long Terminal Repeat during Differentiation of Human Myeloid Cells Is Mediated through Its Transcriptional Enhancer," *Mol. Cell. Biol.*, 9:3571-3575, 1989.
Renan, "Cancer genes: current status, future prospects, and applications in radiotherapy/oncology," *Radiother. Oncol.*, 19:197-218, 1990.
Resendez Jr. et al., "Identification of Highly Conserved Regulatory Domains and Protein-Binding Sites in the Promoters of the Rat and Human Genes Encoding the Stress-Inducible 78-Kilodalton Glucose-Regulated Protein," *Mol. Cell. Biol.*, 8:4579-4584, 1988.
Rich et al., "Development and Analysis of Recombinant Adenoviruses for Gene Therapy of Cystic Fibrosis," *Hum. Gene Ther.*, 4:461-476, 1993.
Ridgeway, In: Vectors: A survey of molecular cloning vectors and their uses, Stoneham: Butterworth, pp. 467-492, 1988.
Rippe et al., Regulatory Elements in the 5'-Flanking Region and the First Intron Contribute to Transcriptional Control of the Mouse Alpha 1 Type I Collagen Gene *Mol. Cell. Biol.*, 9:2224-2227, 1989.
Rippe et al., "DNA-Mediated Gene Transfer into Adult Rat Hepatocytes in Primary Culture," *Mol. Cell. Biol.*, 10:689-695, 1990.
Rittling et al., "AP-1/jun binding sites mediate serum inducibility of the human vimentin promoter," *Nuc. Acids Res.*, 17:1619, 1989.
Rosen et al., "The location of cis-acting regulatory sequences in the human T cell lymphotropic virus type III (HTLV-III/LAV) long terminal repeat," *Cell*, 41:(3):813-823, 1985.
Rosenfeld et al., "Adenovirus-mediated transfer of a recombinant alpha 1-antitrypsin gene to the lung epithelium in vivo," Science, 252:431-434,1991.
Rosenfeld et al., "In vivo transfer of the human cystic fibrosis transmembrane conductance regulator gene to the airway epithelium," *Cell*, 68:143-155, 1992.
Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acacl. Sci. USA*, 86:9079-9083, 1989.
Sage et al., "A software solution for recording circadian oscillator features in time-lapse live cell microscopy," *Cell. Div.*, 5(17):1-9,
Sakai et al., "Hormone-mediated repression: a negative glucocorticoid response element from the bovine prolactin gene," *Genes and Dev.*, 2:1144, 1988.
Satake et al., "Biological Activities of Oligonucleotides Spanning the F9 Point Mutation within the Enhancer Region of Polyomavirus DNA," *J. Virology*, 62:970-977, 1988.
Schaffner et al., "Redundancy of information in enhancers as a principle of mammalian transcription control," *J. Mol. Biol.*, 201:81, 1988.
Schmidt and Grimm, "CRISPR genome engineering and viral gene delivery: a case of mutual attraction," *Biotechnology Journal*, 10:258-272, 2015.
Schwank et al., "Functional Repair of CFTR by CRISPR/Cas9 in Intestinal Stem Cell Organoids of Cystic Fibrosis Patients," *Cell Stem Cel* 13, 653-658, 2013.
Searle et al., "Building a Metal-Responsive Promoter with Synthetic Regulatory Elements," *Mol. Cell. Biol.*, 5:1480-1489, 1985.
Senis et al., "CRISPR/Cas9-mediated genome engineering: an adeno-associated viral (AAV) vector toolbox," *Biotechnology Journal*, 9:1402-1412, 2014.
Sharp and Marciniak, "HIV TAR: An RNA enhancer?" *Cell*, 59:229-230, 1989.

(56) References Cited

OTHER PUBLICATIONS

Shaul and Ben-Levy, "Multiple nuclear proteins in liver cells are bound to hepatitis B virus enhancer element and its upstream sequences<" *EMBO J.*, 6:1913-1920, 1987.
Sherman et al., "Class II Box Consensus Sequences in the HLA-DRcx Gene: Transcriptional Function and Interaction with Nuclear Proteins," *Mol. Cell. Biol.*, 9:50-56, 1989.
Shimizu-Motohashi et al., "Recent advances in innovative therapeutic approaches for Duchenne muscular dystrophy: from discovery to clinical trials," *Am J Transl Res* 8, 2471-89, 2016.
Sleigh and Lockett, "SV40 enhancer activation during retinoic acid-induced differentiation of F9 embryonal carcinoma cells," *J. EMBO*, 4:3831, 1985.
Spalholz et al., "Transactivation of a bovine papilloma virus transcriptional regulatory element by the E2 gene product," *Cell*, 42:183-191, 1985.
Spandau and Lee, "trans-Activation of Viral Enhancers by the Hepatitis B Virus X Protein," *J. Virology*, 62:427-434, 1988.
Spandidos and Wilkie, "Host-specificities of papillomavirus, Moloney murine sarcoma virus and simian virus 40 enhancer sequences," *EMBO J.*, 2:1193-1199, 1983.
Stephens and Hentschel, "The bovine papillomavirus genome and its uses as a eukaryotic vector," *Biochem. J.*, 248:1-11, 1987.
Sternberg et al., "DNA interrogation by the CRISPR RNA-guided endonuclease Cas9," *Nature*, 507: 62-67, 2014.
Stratford-Perricaudet and Perricaudet, In: Human Gene Transfer, Cohen-Haguenauer and Boiron (Eds.), John Libbey Eurotext, France, pp. 51-61, 1991.
Stratford-Perricaudet et al., "Evaluation of the Transfer Human Adenovirus and Expression in Mice of an Enzyme-Encoding Gene Using a Human Adenovirus Vector," *Hum. Gene. Ther.*, 1:241-256, 1990.
Stuart et al., "Identification of multiple metal regulatory elements in mouse metallothionein-I promoter by assaying synthetic sequences," *Nature*, 317:828-831, 1985.
Sullivan and Peterlin, "Transcriptional enhancers in the HLA-DQ subregion," *Mol. Cell. Biol.*, 7:3315, 1987.
Swartzendruber and Lehman, "Neoplastic differentiation: Interaction of simian virus 40 and polyoma virus with murine teratocarcinoma cells in vitro," *J. Cell. Physiology*, 85:179, 1975.
Tabebordbar et al., "In vivo gene editing in dystrophic mouse muscle and muscle stem cells," *Science* 351, 407-411, 2016.
Takebe et al., "SRot Promoter: an efficient and Versatile Mammalian cDNA Expression System Coposed of the Simian Virus 40 Early Promoter and the R-U5 SEgment of Human T-Cell Leukemia Virus Type 1 Long Terminal Repeat," *Mol. Cell. Biol.*, 8:466-472, 1988.
Tavernier et al., "Deletion mapping of the inducible promoter of human IFN-β gene," *Nature*, 301:634, 1983.
Taylor and Kingston, "Ela Transactivation of Human HSP70 Gene Promoter Substitution Mutants Is Independent of the Composition of Upstream and TATA Elements," *Mol. Cell. Biol.*, 10:176-183, 1990.
Taylor and Kingston, "Factor Substitution in a Human HSP70 Gene Promoter: TATADependent and TATA-Independent Interactions," *Mol. Cell. Biol.*, 10:165-175, 1990.
Taylor et al., "Stimulation of the Human Heat Shock Protein 70 Promoter in Vitro by Simian Virus 40 Large T Antigen*," *J. Biol. Chem.*, 274:16160-16164, 1989.
Temin, In: Gene Transfer, Kucherlapati (Ed.), NY, Plenum Press, pp. 149-188, 1986.
Thiesen et al., "A DNA Element Responsible for the Different Tissue Specificities of Friend and Moloney Retroviral Enhancers," *J. Virology*, 62:614-618, 1988.
Top et al., "Immunization with Live Types 7 and 4 Adenovirus Vaccines. II. Antibody Response and Protective Effect against Acute Respiratory Disease Due to Adenovirus Type 7," *J. Infect. Dis.*, 124:155-160, 1971.
Tóth et al., "Cpf1 nucleases demonstrate robust activity to induce DNA modification by exploiting homology directed repair pathways in mammalian cells," *Biology Direct*11(46):1-14, 2016.
Tronche et al., "Anatomy of the rat albumin promoter," *Mol. Biol. Med.*, 7:173-185, 1990.
Trudel and Constantine, "A 3' enhancer contributes to the stage-specific expression of the human-globin gene," *Genes and Dev.* 6:954-61, 1987.
Tur-Kaspa et al., "Use of Electroporation to Introduce Biologically Active Foreign Genes into Primary Rat Hepatocytes," *Mol. Cell Biol.*, 6:716-718, 1986.
Tyndall et al., "A region of the polyoma virus genome between the replication origin and late protein coding sequences is required in cis for both early gene expression and viral DNA replication," *Nucleic Acids Res.*, 9:6231-6251, 1981.
Urnov et al., "Highly efficient endogenous human gene correction using designed zinc-finger nucleases," Nature 435, 646-651,
Van Deutekom and Van Ommen, "Advances in Duchenne muscular dystrophy gene therapy," *Nat Rev Genet* 4, 774-783, 2003.
van Putten et al., "Low dystrophin levels in heart can delay heart failure in mdx mice," *J Mol Cell Cardiol.*, 69:17-23, 2014.
Vannice and Levinson, "Properties of the human hepatitis B virus enhancer: position effects and cell-type nonspecificity," *J. Virology*, 62:1305-1313, 1988.
Varmus et al., "Retroviruses as mutagens: Insertion and excision of a nontransforming provirus alter expression of a resident transforming provirus," *Cell*, 25:23-36, 1981.
Vasseur et al., "Isolation and characterization of polyoma virus mutants able to develop in embryonal carcinoma cells," *Proc Natl. Acad. Sci. USA.*, 77:1068-1072, 1980.
Wagner et al., "Transferrin-polycation conjugates as carriers for DNA uptake into cells," *Proc. Natl. Acad. Sci. USA*, 87(9):3410-3414, 1990.
Walmsley et al., "A Duchenne Muscular Dystrophy Gene Hot Spot Mutation in Dystrophin-Deficient Cavalier King Charles Spaniels Is Amenable to Exon 51 Skipping," *PLoS One*, 5(1):e8647, 2010.
Wang and Calame, "SV40 enhancer-binding factors are required at the establishment but not the maintenance step of enhancer-dependent transcriptional activation," *Cell*, 47:241247, 1986.
Wang et al., "One-Step Generation of Mice Carrying Mutations in Multiple Genes by CRISPR/Cas-Mediated Genome Engineering," *Cell*, 153:910-918, 2013.
Weber et al., "An SV40 "enhancer trap" incorporates exogenous enhancers or generates enhancers from its own sequences," *Cell*, 36:983-992, 1984.
Weinberger et al. "Localization of a Repressive Sequence Contributing to B-Cell Specificity in the Immunoglobulin Heavy-Chain Enhancer," *Mol. Cell. Biol.*, 8:988-992, 1984.
Winoto and Baltimore, "αβ lineage-specific expression of the α T cell receptor gene by nearby silencers," *Cell*, 59:649, 1989.
Wojtal et al., "Spell checking nature: versatility of CRISPR/Cas9 for developing treatments for inherited disorders," *Am. J. Hum. Genet.*, 98(1):90-101, 2016.
Wong et al., "Appearance of β-lactamase activity in animal cells upon liposome-mediated gene transfer," *Gene*, 10:87-94, 1980.
Worton et al., "Genetics of Duchenne Muscular Dystrophy," *Annu Rev Genet* 22, 601-629, 1988.
Wu and Wu, "Evidence for targeted gene delivery to Hep G2 hepatoma cells in vitro," *Biochemistry*, 27:887-892, 1988.
Wu and Wu, "Liver-directed gene delivery," *Adv. Drug Delivery Rev.*, 12:159-167, 1993.
Wu and Wu, "Receptor-mediated in vitro gene transformation by a soluble DNA carrier system," *J. Biol. Chem.*, 262:4429-4432, 1987.
Wu et al., "Correction of a genetic disease in mouse via use of CRISPR-Cas9," *Cell Stem Cell*, 13:659-662, 2013.
Wu et al., "Genome-wide binding of the CRISPR endonuclease Cas9 in mammalian cells," *Nat Biotechnol* 32, 670-676, 2014.
Xu et al., "CRISPR-mediated genome editing restores dystrophin expression and function in mdx mice," *Mol Ther.*, 24(3):564-569, 2016.
Yamauchi-Takihara et al., "Characterization of human cardiac myosin heavy chain genes," *Proc. Natl. Acad. Sci. USA*, 86(101):3504-3508, 1989.
Yang et al., Proc. "In vivo and in vitro gene transfer to mammalian somatic cells by particle bombardment," *Natl. Acad. Sci. USA*, 87:9568-9572, 1990.

(56) References Cited

OTHER PUBLICATIONS

Yen et al., "Somatic mosaicism and allele complexity induced by CRISPR/Cas9 RNA injections in mouse zygotes," *Dev Biol*, published online (10.1016/j.ydbio.2014.06.017), 2014.

Yin et al., "Genome editing with Cas9 in adult mice corrects a disease mutation and phenotype," *Nat. Biotechnol*, 32(6):551-553, 2014.

Yin et al., "Satellite Cells and the Muscle Stem Cell Niche," *Physiol Rev* 93, 23-67, 2013.

Young et al., "A single CRISPR-Cas9 deletion strategy that targets the majority of DMD patients restores dystrophin function in hiPSC-derived muscle cells," *Cell Stem Cell*, 18:533-540, 2016.

Yu et al., "Dystrophin-deficient large animal models: translational research and exon skipping," *Am. J. Transl. Res.*, 7(8):1314-1331, Yu Zhang et al: "CRISPR-Cpf1 correction of muscular dystrophy mutations in human cardiomyocytes and mice," *Science*, vol. 3, No. 4, 12 Apr. 12, 2017 (Apr. 12, 2017), p. 1602814, XP055454449

Yuda Wei et al: "Prevention of Muscle Wasting by CRISPR/Cas9-mediated Disruption of Myostatin in Vivo," Molecular Therapy: The Journal of American Society of Gene Therapy, vol. 24, No. 11, Nov. 1, 2016 (Nov. 1, 2016), pp. 1889-1891, XP055460686.

Yutzey et al., "An Internal Regulatory Element Controls Troponin I Gene Expression," *Mol. Cell. Biol.*, 9:1397, 1989.

Zangi et al., "Modified mRNA directs the fate of heart progenitor cells and induces vascular regeneration after myocardial infarction," *Nat Biotechnol* 31, 898-907, 2013.

Zechner et al., "Total Skeletal Muscle PGC-1 Deficiency Uncouples Mitochondrial Derangements from Fiber Type Determination and Insulin Sensitivity," *Cell Metabolism* 12, 633-642, 2010.

Zelenin et al., "High-velocity mechanical DNA transfer of the chloramphenicolacetyl transferase gene into rodent liver, kidney and mammary gland cells in organ explaintx and in vivo," *FEBS Lett.*, 280:94-96, 1991.

Zetsche et al., "Cpf1 Is a Single RNA-Guided Endonuclease of a Class 2 CRISPR-Cas System," *Cell* 163, 759-771, 2015.

Ziober and Kramer, "Identification and Characterization of the Cell Type-specific and Developmentally Regulated a7 Integrin Gene Promoter," *J. Bio. Chem.*, 271(37):22915-22922, 1996.

\* cited by examiner

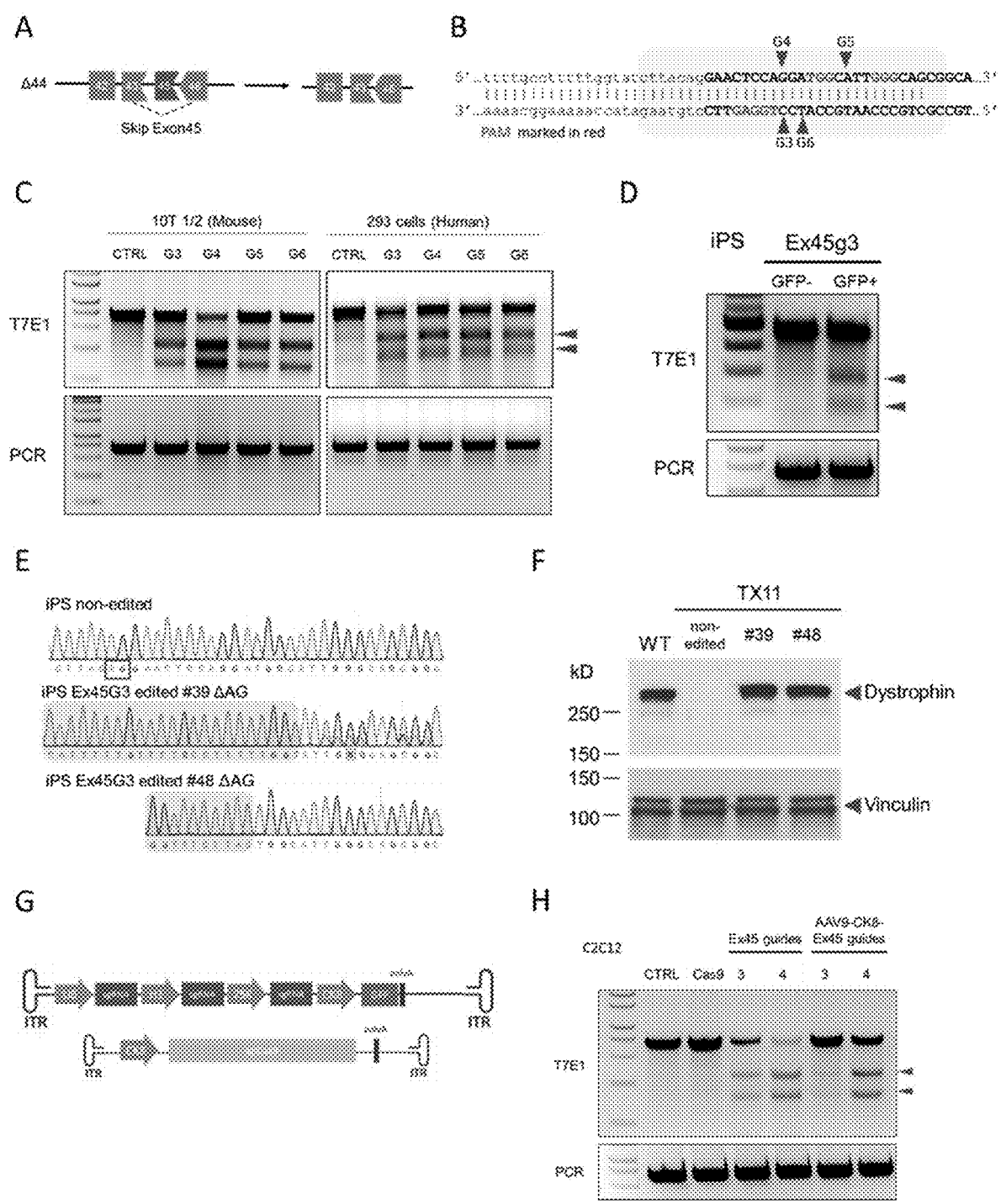
FIGS. 1A-H

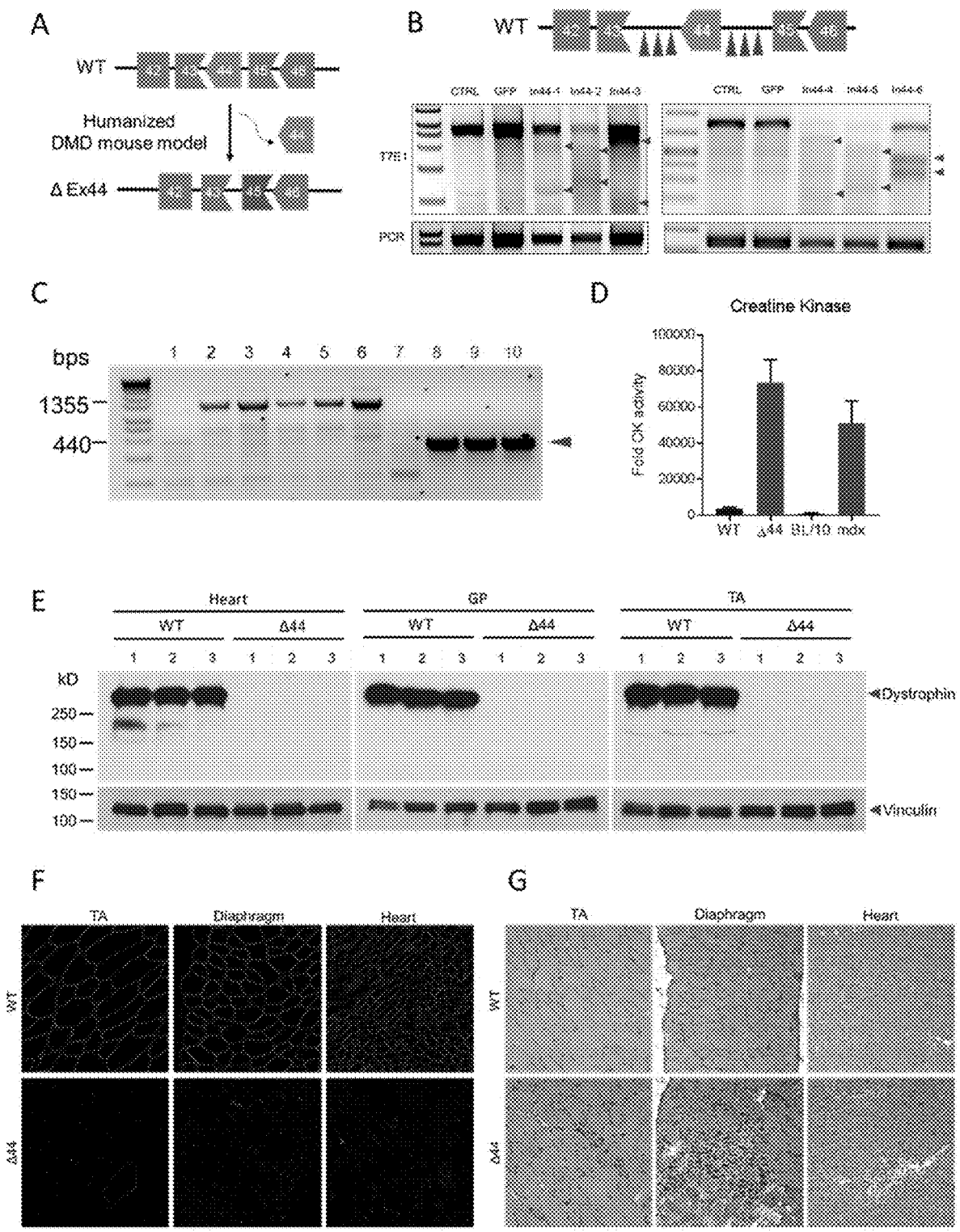
FIGS. 2A-G

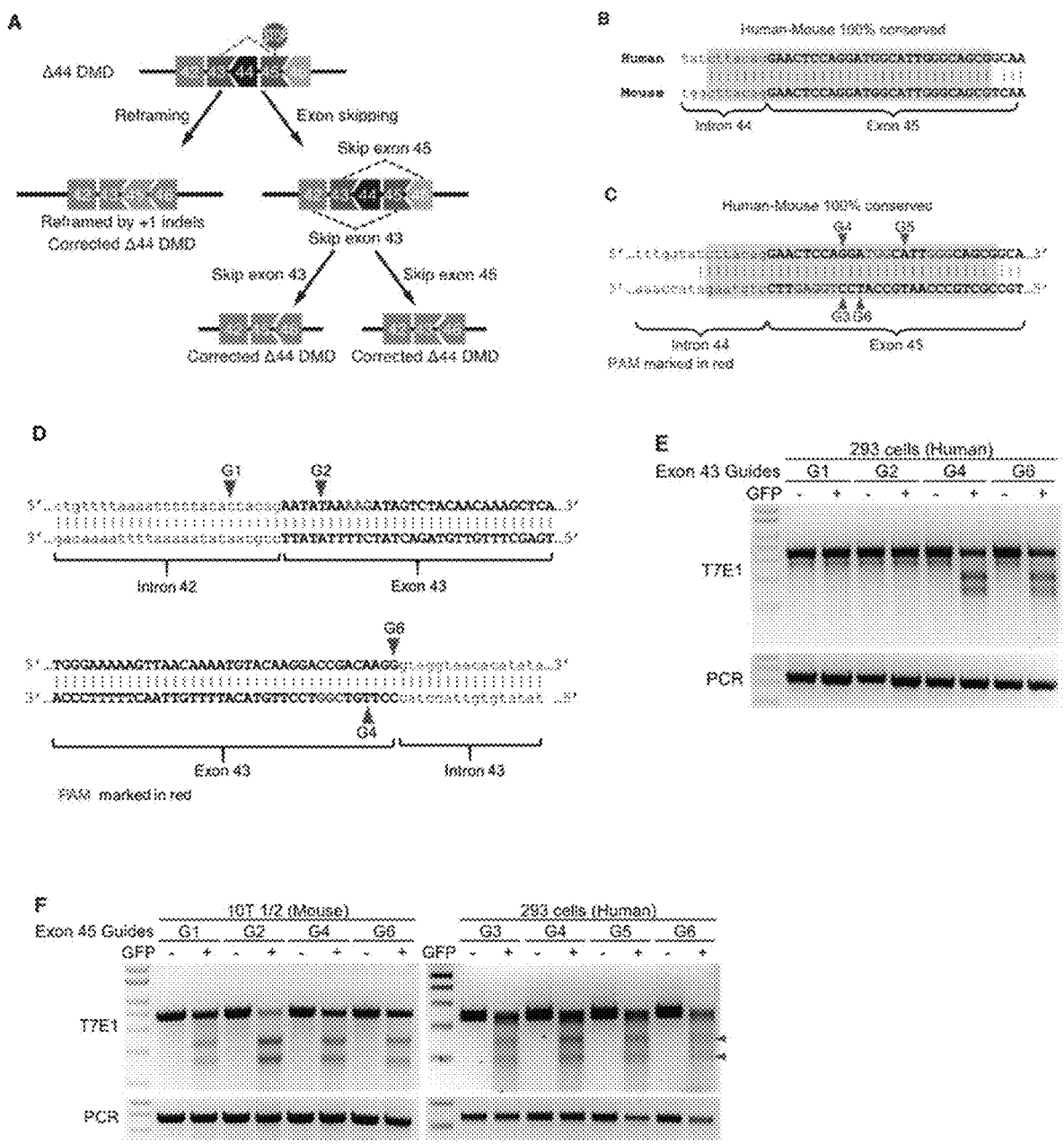
FIGS. 3A-F

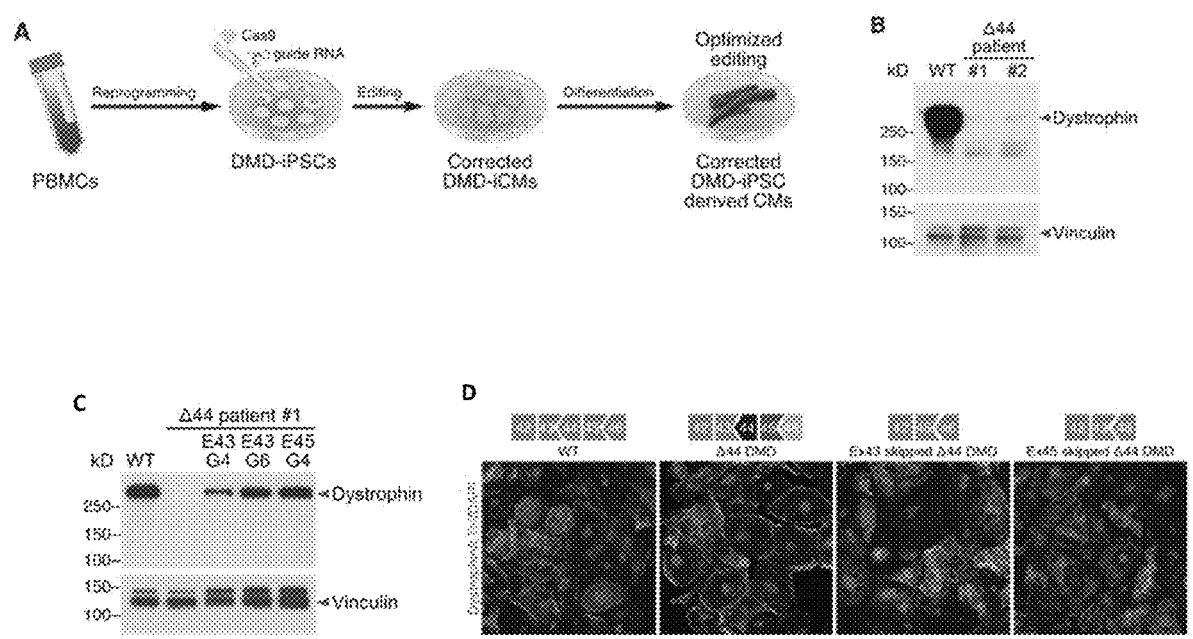
FIGS. 4A-D

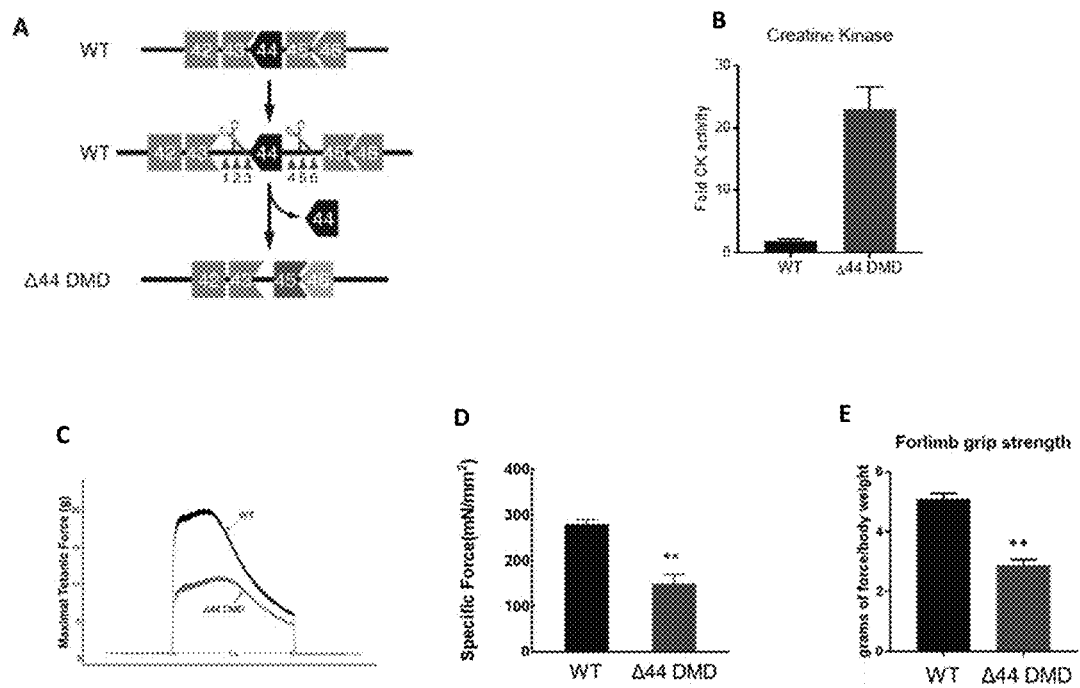
FIGS. 5A-E

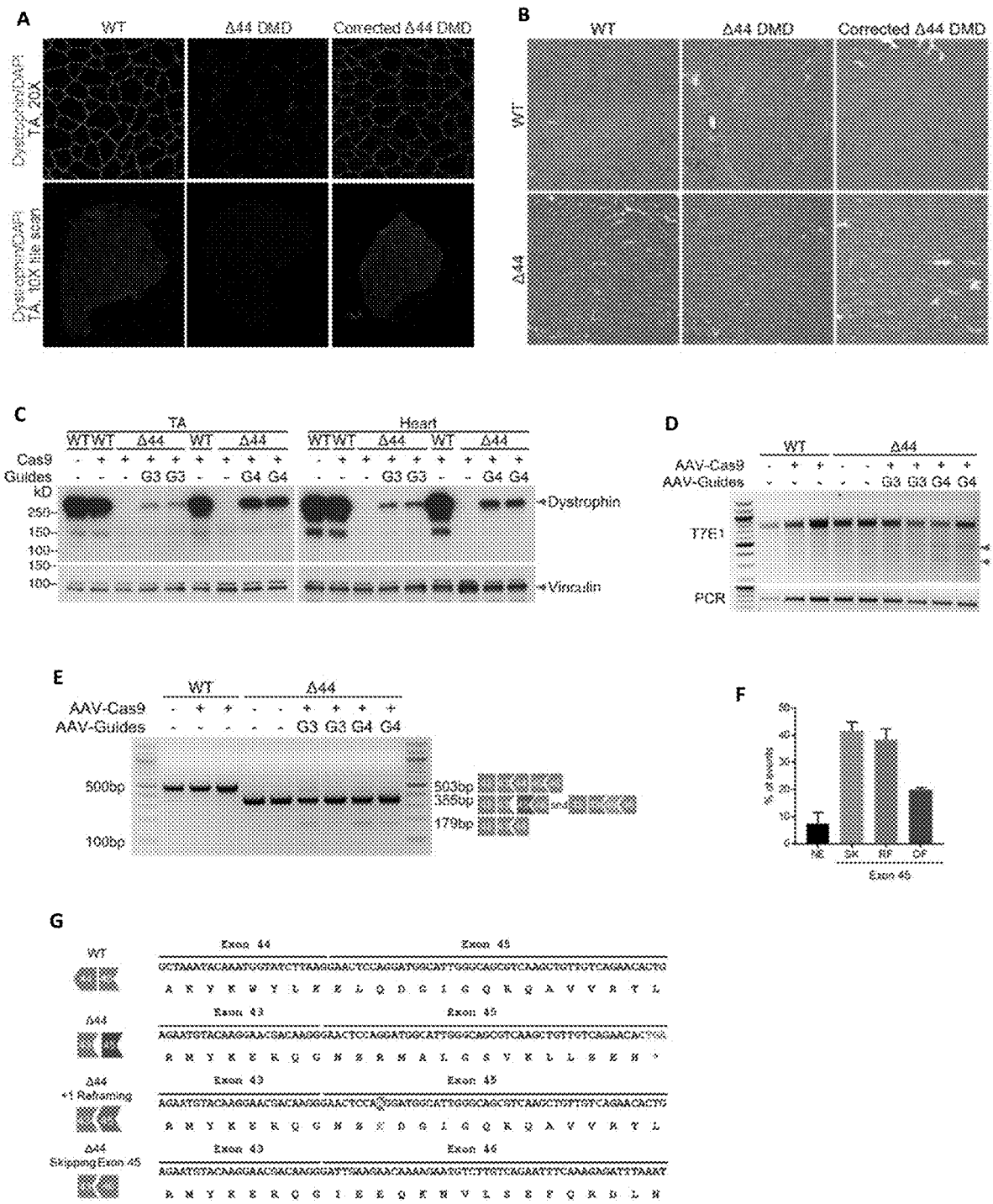
FIGS. 6A-G

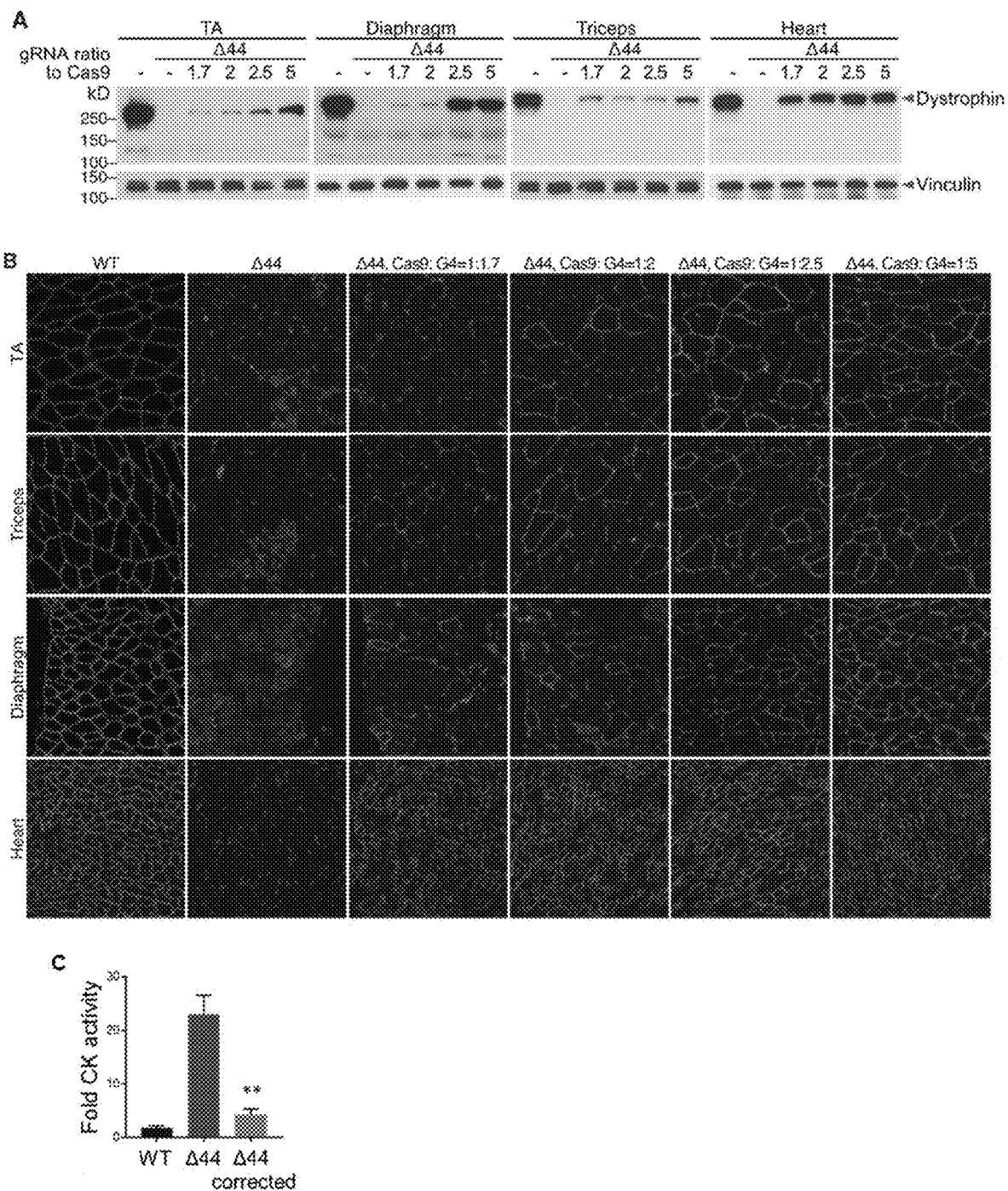
FIGS. 7A-C

GENERATION AND CORRECTION OF A HUMANIZED MOUSE MODEL WITH A DELETION OF DYSTROPHIN EXON 44

PRIORITY CLAIM

The present application claims benefit of priority to U.S. Provisional Application Ser. No. 62/468,154, filed Mar. 7, 2017, the entire contents of which are hereby incorporated by reference in their entirety.

FEDERAL FUNDING SUPPORT CLAUSE

This invention was made with government support under grant no. U54 HD 087351 awarded by National Institutes of Health. The government has certain rights in the invention.

SEQUENCE LISTING

The instant application contains a Sequence Listing, which has been submitted electronically in ASCII format and is hereby incorporated by reference in its entirety. Said ASCII copy, created on Mar. 7, 2018, is named UTSDP3136US.txt and is 16,974 bytes in size.

FIELD OF THE DISCLOSURE

The present disclosure relates to the fields of molecular biology, medicine and genetics. More particularly, the disclosure relates to the use of genome editing to create humanized animal models for different forms of Duchenne muscular dystrophy (DMD), each containing distinct DMD mutations.

BACKGROUND

Muscular dystrophies (MD) are a group of more than 30 genetic diseases characterized by progressive weakness and degeneration of the skeletal muscles that control movement. Duchenne muscular dystrophy (DMD) is one of the most severe forms of MD that affects approximately 1 in 5000 boys and is characterized by progressive muscle weakness and premature death. Cardiomyopathy and heart failure are common, incurable and lethal features of DMD. The disease is caused by mutations in the gene encoding dystrophin (DMD), a large intracellular protein that links the dystroglycan complex at the cell surface with the underlying cytoskeleton, thereby maintaining integrity of the muscle cell membrane during contraction. Mutations in the dystrophin gene result in loss of expression of dystrophin causing muscle membrane fragility and progressive muscle wasting.

Despite intense efforts to find cures through a variety of approaches, including myoblast transfer, viral delivery, and oligonucleotide-mediated exon skipping, there remains no cure for any type of muscular dystrophy. The present inventors recently used clustered regularly interspaced short palindromic repeat/Cas9 (CRISPR/Cas9)-mediated genome editing to correct the dystrophin gene (DMD) mutation in postnatal mdx mice, a model for DMD. In vivo AAV-mediated delivery of gene-editing components successfully removed the mutant genomic sequence by exon skipping in the cardiac and skeletal muscle cells of mdv mice. Using different modes of AAV9 delivery, the inventors restored dystrophin protein expression in cardiac and skeletal muscle of mdx mice. The mdx mouse model and the correction exon 23 using AAV delivery of myoediting machinery has been useful to show proof-of concept of exon skipping approach using several cuts in genomic region encompassing the mutation in vivo. Recent work with ΔEx50 mouse model demonstrated an optimized the method for dystrophin reading frame correction using a single guide RNA that created reframing mutations and allowed permanent skipping of exon 51. However, there is a lack of other models for the various known DMD mutations, and for new mutations that continue to be discovered.

SUMMARY

Thus, in accordance with the present disclosure, there is provided a mouse whose genome comprises a deletion of exon 44 of the dystrophin gene resulting in an out of frame shift and a premature stop codon in exon 45. These mice are highly useful because they contain the second most prominent dystrophin mutation in human, representing ~12% of patients with DMD. The genome of the mouse may further comprise a reporter gene located downstream of and in frame with exon 79 of the dystrophin gene, and upstream of a dystrophin 3'-UTR, wherein said reporter gene is expressed when exon 79 is translated in frame with exon 46. The reporter gene may be luciferase. The genome of the mouse may further comprise a protease coding sequence upstream of and in frame with said reporter gene, and downstream of and in frame with exon 79. The protease may be autocatalytic, such as 2A protease. The mouse may be heterozygous for said deletion, or homozygous for said deletion. The mouse may exhibit increased creatine kinase levels, and/or may not exhibit detectable dystrophin protein in heart or skeletal muscle.

Also provided is a method of producing the mouse described above comprising (a) contacting a fertilized oocyte with CRISPR/Cas9 elements and two single guide RNA (sgRNA) targeting sequences flanking exon 44, thereby creating a modified oocyte, wherein deletion of exon 44 by CRISPR/Cas9 results in an out of frame shift and a premature stop codon in exon 45; (b) transferring said modified oocyte into a recipient female. The oocyte genome may comprise a dystrophin gene having a reporter gene located downstream of and in frame with exon 79 of said dystrophin gene, and upstream of a dystrophin 3'-UTR, wherein said reporter gene is expressed when exon 79 is translated in frame with exon 43. The reporter gene may be luciferase. The oocyte genome may further comprise a protease coding sequence upstream of and in frame with said reporter gene, and downstream of and in frame with exon 79. The protease may be autocatalytic, such as 2A protease. The mouse may be heterozygous for said deletion, or homozygous for said deletion. The mouse may exhibit increased creatine kinase levels and/or may not exhibit detectable dystrophin protein in heart or skeletal muscle.

In another embodiment, there is provided an isolated cell obtained from the mouse described above. The genome of the cell may further comprise a reporter gene located downstream of and in frame with exon 79 of the dystrophin gene, and upstream of a dystrophin 3'-UTR, wherein said reporter gene is expressed when exon 79 is translated in frame with exon 43. The reporter gene may be luciferase. The genome of the cell may further comprise a protease coding sequence upstream of and in frame with said reporter gene, and downstream of and in frame with exon 79. The protease may be autocatalytic, such as 2A protease. The cell may be heterozygous for said deletion, or homozygous for said deletion.

In a further embodiment, there is provided a mouse produced by a method comprising the steps of (a) contacting a fertilized oocyte with CRISPR/Cas9 elements and two single guide RNA (sgRNA) targeting sequences flanking exon 44, thereby creating a modified oocyte, wherein deletion of exon 44 by CRISPR/Cas9 results in an out of frame shift and a premature stop codon in exon 45; (b) transferring said modified oocyte into a recipient female.

These mice provide an important system for assessing the efficacy of a variety of therapeutic analogues for correction of DMD mutation. In one embodiment, CRISPR/Cas9 can be used to skip exon 45, putting the dystrophin protein back in frame. The mice allow for rapid optimization of the method. In other embodiments, the mice can be used to test exon-skipping oligonucleotides or small molecules or other therapeutic modalities in a "humanized" system. In still a further embodiment, there is provided a method of screening a candidate substance for DMD exon-skipping activity comprising (a) contacting a mouse according to claim 1 with a candidate substance; and (b) assessing in frame transcription and/or translation of exon 79, wherein the presence of in frame transcription and/or translation of exon 79 indicates said candidate substance exhibits exon-skipping activity.

A further embodiment comprises an isolated nucleic acid comprising a sequence as set forth below:

| ID | Sequence (5'-3') | SEQ ID NO. |
|---|---|---|
| Ex45-gRNA#3-Top | CACCGCGCTGCCCAATGCCATCCTG | 1 |
| Ex45-gRNA#3-Bot | AAACCAGGATGGCATTGGGCAGCGC | 2 |
| Ex45-gRNA#4-Top | CACCGCTTACAGGAACTCCAGGA | 3 |
| Ex45-gRNA#4-Bot | AAACTCCTGGAGTTCCTGTAAGC | 4 |
| Ex45-gRNA#5-Top | CACCGAGGAACTCCAGGATGGCATT | 5 |
| Ex45-gRNA#5-Bot | AAACAATGCCATCCTGGAGTTCCTC | 6 |
| Ex45-gRNA#6-Top | CACCGCGCTGCCCAATGCCATCC | 7 |
| Ex45-gRNA#6-Bot | AAACGGATGGCATTGGGCAGCGC | 8 |
| Ex45-gRNA#4-mDmd-20-Top | CACCGGCTTACAGGAACTCCAGGA | 27 |
| Ex45-gRNA#4-mDmd-20-Bot | AAACTCCTGGAGTTCCTGTAAGCC | 28 |
| Ex45-gRNA#4-DMD-20-Top | CACCGATCTTACAGGAACTCCAGGA | 29 |
| Ex45-gRNA#4-DMD-20-Bot | AAACTCCTGGAGTTCCTGTAAGATC | 30 |
| Ex43-gRNA#1-DMD-Top | CACCGTTTTAAAATTTTTATATTA | 31 |
| Ex43-gRNA#1-DMD-Bot | AAACTAATATAAAAATTTTAAAAC | 32 |
| Ex43-gRNA#2-DMD-Top | CACCGTTTTATATTACAGAATATAA | 33 |
| Ex43-gRNA#2-DMD-Bot | AAACTTATATTCTGTAATATAAAAC | 34 |
| Ex43-gRNA#4-DMD-Top | CACCGTATGTGTTACCTACCCTTGT | 35 |
| Ex43-gRNA#4-DMD-Bot | AAACACAAGGGTAGGTAACACATAC | 36 |
| Ex43-gRNA#6-DMD-Top | CACCGTACAAGGACCGACAAGGGT | 37 |
| Ex43-gRNA#6-DMD-Bot | AAACACCCTTGTCGGTCCTTGTAC | 38 |

Also provided is a double-stranded nucleic acid formed by hybridization of SEQ ID NO: 1 and 2, SEQ ID NO: 3 and 4, SEQ ID NO: 5 and 6, SEQ ID NO: 7 and 8, SEQ ID NO: 27 and 28, SEQ ID NO: 29 and 30, SEQ ID NO: 31 and 32, SEQ ID NO: 33 and 34, SEQ ID NO: 35 and 36, or SEQ ID NO: 37 and 38, and an expression construct comprising a nucleic acid formed by hybridization of SEQ ID NO: 1 and 2, SEQ ID NO: 3 and 4, SEQ ID NO: 5 and 6, SEQ ID NO: 7 and 8, SEQ ID NO: 27 and 28, SEQ ID NO: 29 and 30, SEQ ID NO: 31 and 32, SEQ ID NO: 33 and 34, SEQ ID NO: 35 and 36, SEQ ID NO: 37 and 38, such as a viral or non-viral vector. Additionally, a kit comprising one or more isolated nucleic acids as set forth below is described:

| ID | Sequence (5'-3') | SEQ ID NO. |
|---|---|---|
| Ex45-gRNA#3-Top | CACCGCGCTGCCCAATGCCATCCTG | 1 |
| Ex45-gRNA#3-Bot | AAACCAGGATGGCATTGGGCAGCGC | 2 |
| Ex45-gRNA#4-Top | CACCGCTTACAGGAACTCCAGGA | 3 |
| Ex45-gRNA#4-Bot | AAACTCCTGGAGTTCCTGTAAGC | 4 |
| Ex45-gRNA#5-Top | CACCGAGGAACTCCAGGATGGCATT | 5 |
| Ex45-gRNA#5-Bot | AAACAATGCCATCCTGGAGTTCCTC | 6 |
| Ex45-gRNA#6-Top | CACCGCGCTGCCCAATGCCATCC | 7 |
| Ex45-gRNA#6-Bot | AAACGGATGGCATTGGGCAGCGC | 8 |
| Ex45-gRNA#4-mDmd-20-Top | CACCGGCTTACAGGAACTCCAGGA | 27 |
| Ex45-gRNA#4-mDmd-20-Bot | AAACTCCTGGAGTTCCTGTAAGCC | 28 |
| Ex45-gRNA#4-DMD-20-Top | CACCGATCTTACAGGAACTCCAGGA | 29 |
| Ex45-gRNA#4-DMD-20-Bot | AAACTCCTGGAGTTCCTGTAAGATC | 30 |
| Ex43-gRNA#1-DMD-Top | CACCGTTTTAAAATTTTTATATTA | 31 |
| Ex43-gRNA#1-DMD-Bot | AAACTAATATAAAAATTTTAAAAC | 32 |
| Ex43-gRNA#2-DMD-Top | CACCGTTTTATATTACAGAATATAA | 33 |
| Ex43-gRNA#2-DMD-Bot | AAACTTATATTCTGTAATATAAAAC | 34 |
| Ex43-gRNA#4-DMD-Top | CACCGTATGTGTTACCTACCCTTGT | 35 |
| Ex43-gRNA#4-DMD-Bot | AAACACAAGGGTAGGTAACACATAC | 36 |
| Ex43-gRNA#6-DMD-Top | CACCGTACAAGGACCGACAAGGGT | 37 |
| Ex43-gRNA#6-DMD-Bot | AAACACCCTTGTCGGTCCTTGTAC | 38 | or an expression vector coding therefor.

Still a further embodiment comprises a method of correcting a dystrophin gene defect in Exon 45 of the DMD gene in a subject comprising contacting a cell in said subject with Cpf1 or Cas9 and a DMD guide RNA as defined above, resulting in selective skipping of a mutant DMD exon. The cell may be a muscle cell, a satellite cell, or an iPSC/iCM. Cpf1 and/or DMD guide RNA may be provided to said cell through expression from one or more expression vectors coding therefor, such as a viral vector (e.g., adeno-associated viral vector) or as a non-viral vector. Cpf1 or Cas9 may be provided to said cell as naked plasmid DNA or chemically-modified mRNA.

The method may further comprise contacting said cell with a single-stranded DMD oligonucleotide to effect homology directed repair or non-homologous end joining (NHEJ). Cpf1 or Cas9, DMD guide RNA and/or single-stranded DMD oligonucleotide, or expression vectors coding therefor, may be provided to said cell in one or more nanoparticles. Cpf1 or Cas9, DMD guide RNA and/or single-stranded DMD oligonucleotide may be delivered directly to a muscle tissue, such as tibialis anterior, quadricep, soleus, diaphragm or heart. Cpf1 or Cas9, DMD guide RNA and/or single-stranded DMD oligonucleotide may be delivered systemically.

The subject may exhibit normal dystrophin-positive myofibers and/or mosaic dystrophin-positive myofibers containing centralized nuclei. The subject may exhibit a decreased serum CK level as compared to a serum CK level prior to contacting. The subject may exhibit improved grip strength as compared to a serum CK level prior to contacting. The correction may be permanent skipping of said mutant DMD exon, or more than one mutant DMD exon. The Cpf1 or Cas9 and/or DMD guide RNA may be delivered to a human iPS cell with an adeno-associated viral vector.

It is contemplated that any method or composition described herein can be implemented with respect to any other method or composition described herein.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

The patent or application file contains at least one drawing executed in color. Copies of this patent or patent application publication with color drawing(s) will be provided by the Office upon request and payment of the necessary fee.

FIGS. 1A-H. Exon 44 deleted DMD patient iPSC-derived cardiomyocytes express dystrophin after CRISPR/Cas9 mediated genome editing by exon skipping. (FIG. 1A) A DMD deletion of exon 44 results in splicing of exon 43 to 45, generating an out-of-frame mutation of dystrophin. Disruption of the splice acceptor of exon 45 results in splicing of exon 43 to 46 and restoration of the protein reading frame. (FIG. 1B) Illustration of sgRNAs targeting exon 45 splice acceptor site. The PAM (red) of the sgRNAs is located near the exon45 splice acceptor site. The 100% human and mouse conserved sequence is shaded in light yellow. Exon sequence is bold upper case. Intron sequence is lower case. (SEQ ID NOS: 22-23) (FIG. 1C) T7E1 assay using 10T½ mouse cells and 293 human cells transfected with spCas9 and exon45 sgRNA3 (G3), sgRNA4 (G4), sgRNA5 (G5) or sgRNA6 (G6) shows cleavage of the DMD locus at intron-exon junction of exon45. Red arrowheads denote cleavage products. (FIG. 1D) T7E1 assay using iPS cells transfected with spCas9 and exon 45 sgRNA3 (G3) shows cleavage of the DMD locus at intron-exon junction of exon45. Red arrowheads denote cleavage products. (FIG. 1E) PCR products of genomic DNA isolated from single clones of exon 44 deleted DMD-iPSCs transfected with a plasmid expressing spCas9 and exon 45 sgRNA3 (G3). Sequence of the PCR products of each clone shows deletions from the 3'-end of intron 44 to the 5'-end of exon 45. This confirms removal of the "ag" splice acceptor of exon 45. The sequence of the uncorrected allele is shown above that of the exon 45-skipped allele. (SEQ ID NOS: 24-26) (FIG. 1F) Western blot analysis shows restoration of dystrophin expression in exon 45-skipped single clones. Vinculin was used as a loading control. (FIG. 1G) Illustration of an AAV9 plasmid encoding three spCas9 sgRNAs driven by the U6, H1, and 7SK promoters. The plasmid also encodes a GFP driven by CK8 promoter. A separate AAV9 plasmid encodes spCas9 driven by CK8 promoter. (FIG. 1H) T7E1 assay using C2C12 mouse cells transfected with spCas9 and exon 45 sgRNA3 (G3), exon 45 sgRNA4 (G4), AAV9-CK8-exon 45 sgRNA3 or sgRNA4 shows cleavage of the DMD locus at intron-exon junction of exon45. Red arrowheads denote cleavage products.

FIGS. 2A-G. "Humanized"-ΔEx44 mouse model. (FIG. 2A) Outline of the CRISPR/Cas9 strategy used for generation of the mice. (FIG. 2B) Outline of the CRISPR/Cas9 strategy to deplete exon 44. T7E1 assay using 10T½ mouse cells transfected with spCas9 with different sgRNAs targeting 5' end (In44-1, In44-2 or In44-3) and 3' end (In44-4, In44-5, In44-6) of exon 44 shows different cleavage efficiency at the Dmd exon 44. Red arrowheads show cleavage products of genome editing. (FIG. 2C) PCR genotyping of 10 F1 pups shows efficient exon 44 depletion by CRISPR/Cas9-mediated genome editing. The lower band (red arrowheads) shows exon44 deletion. (FIG. 2D) Serum creatine kinase (CK), a marker of muscle dystrophy that reflects muscle damage and membrane leakage was measured in wild type (WT), ΔEx44, BL/10 and mdx mice. (FIG. 2E) Western blot analysis shows loss of dystrophin expression in heart, TA muscle, and gastrocnemius/plantaris (G/P) muscle of ΔEx44 mice. Vinculin was used as a loading control. (FIG. 2F) Dystrophin staining of TA, diaphragm and cardiac muscle. (FIG. 2G) Hematoxylin and eosin (H&E) staining of TA, diaphragm and cardiac muscle.

FIGS. 3A-F. Identification of optimal sgRNAs for CRISPR/Cas9 correction of DMD Exon 44 deletions. (FIG. 3A) A DMD deletion of exon 44 results in splicing of exon 43 to 45, generating an out-of-frame mutation of dystrophin. Disruption of the splice junction of exon 43 or exon 45 results in splicing of exon 42 to 45 or exon 43 to 46 and restoration of the protein reading frame. Alternatively, gene editing results in restoration of the protein reading frame. (FIG. 3B) Illustration of the 100% human and mouse conserved sequence at the intron-exon junction of exon 45. The conserved region is shaded in light blue. FIG. 3B discloses SEQ ID NOS 55-56, respectively, in order of appearance. (FIG. 3C) Illustration of sgRNAs targeting exon 45 splice acceptor site. The PAM (red) of the sgRNAs is located near the exon45 splice acceptor site. The 100% human and mouse conserved sequence is shaded in light blue. Exon sequence is bold upper case. Intron sequence is lower case. FIG. 3C discloses SEQ ID NO: 57. (FIG. 3D) Illustration of sgRNAs targeting exon 43 splice acceptor and donor site. The PAM (red) of the sgRNAs is located near the exon43 splicing junctions. Exon sequence is bold upper case. Intron sequence is lower case. FIG. 3D discloses SEQ ID NOS 58-59, respectively, in order of appearance. (FIG. 3E) T7E1 assay using 293 human cells transfected with spCas9 and exon43 sgRNA1 (G1), sgRNA2 (G2), sgRNA4 (G4) or sgRNA6 (G6) shows cleavage of the DMD locus at intron-exon junctions of exon43. Red arrowheads denote cleavage products. (FIG. 3F) T7E1 assay using 10T½ mouse cells and 293 human cells transfected with spCas9 and exon45 sgRNA3 (G3), sgRNA4 (G4), sgRNA5 (G5) or sgRNA6 (G6) shows cleavage of the DMD locus at intron-exon junction of exon45. Red arrowheads denote cleavage products.

FIGS. 4A-D. Exon 44 deleted DMD patient iPSC-derived cardiomyocytes express dystrophin after CRISPR/Cas9 mediated genome editing by exon skipping (FIG. 4A) Schematic of the procedure for derivation and editing of patient-derived iPSCs. (FIG. 4B) Western blot analysis shows absence of dystrophin in cardiomyocytes differentiated from two patient-derived iPSCs. (FIG. 4C) Western blot analysis shows restoration of dystrophin expression in exon 45-edited and exon 43-edited cells. Vinculin is loading control. (FIG. 4D) Immunostaining shows restoration of dystrophin expression in exon 45-edited and exon 43-edited cells. Dystrophin stains in red. Cardiac troponinI stains in green. Nucleus marks by DAPI stains in blue.

FIGS. 5A-E. Characterization of ΔEx44 mice. (FIG. 5A) Outline of the CRISPR/Cas9 strategy used for generation of the mice. (FIG. 5B) Activity of serum creatine kinase (CK), a marker of muscle dystrophy that reflects muscle damage and membrane leakage was measured in wild type (WT) and ΔEx44 mice. Maximal tetanic force (FIG. 5C), specific force (FIG. 5D), and forelimb grip strength (FIG. 5E) were reduced in ΔEx44 mice compared to wild type (WT) mice, indicating decreased muscle function.

FIGS. 6A-G. Correction of DMD exon 44 deletion in mice by intramuscular AAV9 delivery of gene editing components. (FIG. 6A) Immunostaining shows restoration of dystrophin in TA muscle of Δ44 mice 3 weeks after intramuscular injection of gene editing component carried by AAV9. Dystrophin stains in red. Nucleus marks by DAPI stains in blue. (FIG. 6B) Hematoxylin and eosin (H&E) staining of TA and cardiac muscles in wildtype (WT), Δ44, and corrected Δ44 mice. (FIG. 6C) Western blot analysis shows restoration of dystrophin expression in TA muscle and heart of Δ44 mice. Vinculin is loading control. (FIG. 6D) T7E1 assay shows cleavage of the DMD locus at intron-exon junction of exon45 in TA muscle of corrected Δ44 mice. Red arrowheads show cleavage products of genome editing. (FIG. 6E) RT-PCR analysis of the TA muscles from WT, Δ44 and Δ44 mice 3 weeks after intramuscular injection of gene editing component carried by AAV9. Lower dystrophin bands indicate skipping of exon 45. (FIG. 6F) Percentage of events detected at exon 45 after AAV9-Cas9/exon45-sgRNA4 treatment using RT-PCR sequence analysis of TOPO-TA (topoisomerase-based thymidine to adenosine) generated clones. RT-PCR products are divided into four groups: Not edited (NE), exon 45-skipped (SK), reframed (RF), and out-of-frame (OF). (FIG. 6G) Sequence of the RT-PCR products of the WT, Δ44 and corrected Δ44 mice. Both exon 45-skipped and +1 reframed sequences are shown. FIG. 6G discloses SEQ ID NOS 60-67, respectively, in order of appearance.

FIGS. 7A-C. Systemic AAV9 delivery of gene editing components to Δ44 mice rescues dystrophin expression. Different AAV9-Cas9 and AAV9-exon45-sgRNA4 ratios were injected into Δ44 mice: 1:1.7 ($5\times10^{13}$ vg/kg of AAV9-Cas9 to $8.5\times10^{13}$ vg/kg of AAV9-exon45-sgRNA4); 1:2 ($5\times10^{13}$ vg/kg of AAV9-Cas9 to $1\times10^{14}$ vg/kg of AAV9-exon45-sgRNA4); 1:2.5 $5\times10^{13}$ vg/kg of AAV9-Cas9 to $1.25\times10^{13}$ vg/kg of AAV9-exon45-sgRNA4) and 1:5 ($5\times10^{13}$ vg/kg of AAV9-Cas9 to $2\times10^{14}$ vg/kg of AAV9-exon45-sgRNA4). (FIG. 7A) Western blot analysis shows restoration of dystrophin expression in TA, diaphragm, triceps and cardiac muscles of Δ44 mice 4 weeks after systemic delivery of AAV9-Cas9 or AAV9-Cas9/exon45-sgRNA4. Vinculin was used as a loading control. (FIG. 7B) Immunostaining shows restoration of dystrophin in TA, diaphragm, triceps and cardiac muscles of Δ44 mice 4 weeks after systemic delivery of AAV9-Cas9 or AAV9-Cas9/exon45-sgRNA4. Dystrophin stains in red. Nucleus marks by DAPI stains in blue. (FIG. 7C) Reduction of serum creatine kinase activity in Δ44 mice 4 weeks after systemic delivery of AAV9-Cas9 or AAV9-Cas9/exon45-sgRNA4.

DETAILED DESCRIPTION

DMD is a new mutation syndrome with more than 4,000 independent mutations that have been identified in humans (world-wide web at dmd.nl). The majority of patient's mutations carry deletions that cluster in a hotspot, and thus a therapeutic approach for skipping certain exon applies to large group of patients. The rationale of the exon skipping approach is based on the genetic difference between DMD and Becker muscular dystrophy (BMD) patients. In DMD patients, the reading frame of dystrophin mRNA is disrupted resulting in prematurely truncated, non-functional dystrophin proteins. BMD patients have mutations in the DMD gene that maintain the reading frame allowing the production of internally deleted, but partially functional dystrophins leading to much milder disease symptoms compared to DMD patients.

One the most common hot spots in DMD is the genetic region between exons 44 and 51, where skipping of exon 45 would apply to ~12% of the DMD population. The instant disclosure demonstrates the efficiency of CRISPR/Cas9 mediated correction of DMD mutations in patient-derived iPS cells. To further assess the efficiency and optimize CRISPR/Cas9-mediated exon skipping in vivo, a mimic of the human "hot spot" region was generated in a mouse model by deleting the exon 44 using CRISPR/Cas9 system directed by two single guide RNAs (sgRNAs). The ΔEx44 mouse model exhibits dystrophic myofibers and increased serum creatine kinase level, thus providing a representative model of DMD. These and other aspects of the disclosure are reproduced below.

I. DUCHENNE MUSCULAR DYSTROPHY

A. Background

Duchenne muscular dystrophy (DMD) is a recessive X-linked form of muscular dystrophy, affecting around 1 in 5000 boys, which results in muscle degeneration and premature death. The disorder is caused by a mutation in the gene dystrophin, located on the human X chromosome, which codes for the protein dystrophin. Dystrophin is an important component within muscle tissue that provides structural stability to the dystroglycan complex (DGC) of the cell membrane. While both sexes can carry the mutation, females are rarely affected with the skeletal muscle form of the disease.

Mutations vary in nature and frequency. Large genetic deletions are found in about 60-70% of cases, large duplications are found in about 10% of cases, and point mutants or other small changes account for about 15-30% of cases. Bladen et al. (2015), who examined some 7000 mutations, catalogued a total of 5,682 large mutations (80% of total mutations), of which 4,894 (86%) were deletions (1 exon or larger) and 784 (14%) were duplications (1 exon or larger). There were 1,445 small mutations (smaller than 1 exon, 20% of all mutations), of which 358 (25%) were small deletions and 132 (9%) small insertions, while 199 (14%) affected the splice sites. Point mutations totaled 756 (52% of small mutations) with 726 (50%) nonsense mutations and 30 (2%) missense mutations. Finally, 22 (0.3%) mid-intronic mutations were observed. In addition, mutations were identified within the database that would potentially benefit from novel genetic therapies for DMD including stop codon read-through therapies (10% of total mutations) and exon skipping therapy (80% of deletions and 55% of total mutations).

B. Symptoms

Symptoms usually appear in boys between the ages of 2 and 3 and may be visible in early infancy. Even though symptoms do not appear until early infancy, laboratory testing can identify children who carry the active mutation at birth. Progressive proximal muscle weakness of the legs and pelvis associated with loss of muscle mass is observed first. Eventually this weakness spreads to the arms, neck, and other areas. Early signs may include pseudohypertrophy (enlargement of calf and deltoid muscles), low endurance, and difficulties in standing unaided or inability to ascend staircases. As the condition progresses, muscle tissue experiences wasting and is eventually replaced by fat and fibrotic tissue (fibrosis). By age 10, braces may be required to aid in walking but most patients are wheelchair dependent by age 12. Later symptoms may include abnormal bone development that lead to skeletal deformities, including curvature of the spine. Due to progressive deterioration of muscle, loss of movement occurs, eventually leading to paralysis. Intellectual impairment may or may not be present but if present, does not progressively worsen as the child ages. The average life expectancy for males afflicted with DMD is around 25.

The main symptom of Duchenne muscular dystrophy, a progressive neuromuscular disorder, is muscle weakness associated with muscle wasting with the voluntary muscles being first affected, especially those of the hips, pelvic area, thighs, shoulders, and calves. Muscle weakness also occurs later, in the arms, neck, and other areas. Calves are often enlarged. Symptoms usually appear before age 6 and may appear in early infancy. Other physical symptoms are:

- Awkward manner of walking, stepping, or running— (patients tend to walk on their forefeet, because of an increased calf muscle tone. Also, toe walking is a compensatory adaptation to knee extensor weakness.)
- Frequent falls
- Fatigue
- Difficulty with motor skills (running, hopping, jumping)
- Lumbar hyperlordosis, possibly leading to shortening of the hip-flexor muscles. This has an effect on overall posture and a manner of walking, stepping, or running.
- Muscle contractures of Achilles tendon and hamstrings impair functionality because the muscle fibers shorten and fibrose in connective tissue
- Progressive difficulty walking
- Muscle fiber deformities
- Pseudohypertrophy (enlarging) of tongue and calf muscles. The muscle tissue is eventually replaced by fat and connective tissue, hence the term pseudohypertrophy.
- Higher risk of neurobehavioral disorders (e.g., ADHD), learning disorders (dyslexia), and non-progressive weaknesses in specific cognitive skills (in particular short-term verbal memory), which are believed to be the result of absent or dysfunctional dystrophin in the brain.
- Eventual loss of ability to walk (usually by the age of 12)
- Skeletal deformities (including scoliosis in some cases)
- Trouble getting up from lying or sitting position The condition can often be observed clinically from the moment the patient takes his first steps, and the ability to walk usually completely disintegrates between the time the boy is 9 to 12 years of age. Most men affected with DMD become essentially "paralyzed from the neck down" by the age of 21. Muscle wasting begins in the legs and pelvis, then progresses to the muscles of the shoulders and neck, followed by loss of arm muscles and respiratory muscles. Calf muscle enlargement (pseudohypertrophy) is quite obvious. Cardiomyopathy particularly (dilated cardiomyopathy) is common, but the development of congestive heart failure or arrhythmia (irregular heartbeat) is only occasional.

A positive Gowers' sign reflects the more severe impairment of the lower extremities muscles. The child helps himself to get up with upper extremities: first by rising to stand on his arms and knees, and then "walking" his hands up his legs to stand upright. Affected children usually tire more easily and have less overall strength than their peers. Creatine kinase (CPK-MM) levels in the bloodstream are extremely high. An electromyography (EMG) shows that weakness is caused by destruction of muscle tissue rather than by damage to nerves. Genetic testing can reveal genetic errors in the Xp21 gene. A muscle biopsy (immunohistochemistry or immunoblotting) or genetic test (blood test) confirms the absence of dystrophin, although improvements in genetic testing often make this unnecessary.

- Abnormal heart muscle (cardiomyopathy)
- Congestive heart failure or irregular heart rhythm (arrhythmia)
- Deformities of the chest and back (scoliosis)
- Enlarged muscles of the calves, buttocks, and shoulders (around age 4 or 5). These muscles are eventually replaced by fat and connective tissue (pseudohypertrophy).
- Loss of muscle mass (atrophy)
- Muscle contractures in the heels, legs
- Muscle deformities
- Respiratory disorders, including pneumonia and swallowing with food or fluid passing into the lungs (in late stages of the disease)

C. Causes

Duchenne muscular dystrophy (DMD) is caused by a mutation of the dystrophin gene at locus Xp21, located on the short arm of the X chromosome. Dystrophin is responsible for connecting the cytoskeleton of each muscle fiber to the underlying basal lamina (extracellular matrix), through a protein complex containing many subunits. The absence of dystrophin permits excess calcium to penetrate the sarcolemma (the cell membrane). Alterations in calcium and signaling pathways cause water to enter into the mitochondria, which then burst.

In skeletal muscle dystrophy, mitochondrial dysfunction gives rise to an amplification of stress-induced cytosolic calcium signals and an amplification of stress-induced reactive-oxygen species (ROS) production. In a complex cascading process that involves several pathways and is not clearly understood, increased oxidative stress within the cell damages the sarcolemma and eventually results in the death of the cell. Muscle fibers undergo necrosis and are ultimately replaced with adipose and connective tissue.

DMD is inherited in an X-linked recessive pattern. Females will typically be carriers for the disease while males will be affected. Typically, a female carrier will be unaware they carry a mutation until they have an affected son. The son of a carrier mother has a 50% chance of inheriting the defective gene from his mother. The daughter of a carrier mother has a 50% chance of being a carrier and a 50% chance of having two normal copies of the gene. In all cases, an unaffected father will either pass a normal Y to his son or a normal X to his daughter. Female carriers of an X-linked recessive condition, such as DMD, can show symptoms depending on their pattern of X-inactivation.

Duchenne muscular dystrophy has an incidence of 1 in 5000 male infants. Mutations within the dystrophin gene can either be inherited or occur spontaneously during germline transmission. A table of exemplary but non-limiting mutations and corresponding models are set forth below:

| Deletion, small insertion and nonsense mutations | Name of Mouse Model |
| --- | --- |
| Exon 44 | ΔEx44 |
| Exon 52 | ΔEx52 |
| Exon 43 | ΔEx43 |

D. Diagnosis

Genetic counseling is advised for people with a family history of the disorder. Duchenne muscular dystrophy can be detected with about 95% accuracy by genetic studies.

DNA Test.

The muscle-specific isoform of the dystrophin gene is composed of 79 exons, and DNA testing and analysis can usually identify the specific type of mutation of the exon or exons that are affected. DNA testing confirms the diagnosis in most cases.

Muscle Biopsy.

If DNA testing fails to find the mutation, a muscle biopsy test may be performed. A small sample of muscle tissue is extracted (usually with a scalpel instead of a needle) and a dye is applied that reveals the presence of dystrophin. Complete absence of the protein indicates the condition.

Over the past several years DNA tests have been developed that detect more of the many mutations that cause the condition, and muscle biopsy is not required as often to confirm the presence of Duchenne's.

Prenatal Tests.

DMD is carried by an X-linked recessive gene. Males have only one X chromosome, so one copy of the mutated gene will cause DMD. Fathers cannot pass X-linked traits on to their sons, so the mutation is transmitted by the mother.

If the mother is a carrier, and therefore one of her two X chromosomes has a DMD mutation, there is a 50% chance that a female child will inherit that mutation as one of her two X chromosomes, and be a carrier. There is a 50% chance that a male child will inherit that mutation as his one X chromosome, and therefore have DMD.

Prenatal tests can tell whether their unborn child has the most common mutations. There are many mutations responsible for DMD, and some have not been identified, so genetic testing only works when family members with DMD have a mutation that has been identified.

Prior to invasive testing, determination of the fetal sex is important; while males are sometimes affected by this X-linked disease, female DMD is extremely rare. This can be achieved by ultrasound scan at 16 weeks or more recently by free fetal DNA testing. Chorion villus sampling (CVS) can be done at 11-14 weeks, and has a 1% risk of miscarriage. Amniocentesis can be done after 15 weeks, and has a 0.5% risk of miscarriage. Fetal blood sampling can be done at about 18 weeks. Another option in the case of unclear genetic test results is fetal muscle biopsy.

E. Treatment

There is no current cure for DMD, and an ongoing medical need has been recognized by regulatory authorities. Phase 1-2a trials with exon skipping treatment for certain mutations have halted decline and produced clinical improvements in walking. Sarepta's drug Exondys 51 (eteplirsen) has recently received FDA approval. However, treatment is generally aimed at controlling the onset of symptoms to maximize the quality of life, and include the following:

Corticosteroids such as prednisolone and deflazacort increase energy and strength and defer severity of some symptoms.

Randomized control trials have shown that beta-2-agonists increase muscle strength but do not modify disease progression. Follow-up time for most RCTs on beta2-agonists is only around 12 months and hence results cannot be extrapolated beyond that time frame.

Mild, non-jarring physical activity such as swimming is encouraged. Inactivity (such as bed rest) can worsen the muscle disease.

Physical therapy is helpful to maintain muscle strength, flexibility, and function.

Orthopedic appliances (such as braces and wheelchairs) may improve mobility and the ability for self-care. Form-fitting removable leg braces that hold the ankle in place during sleep can defer the onset of contractures.

Appropriate respiratory support as the disease progresses is important.

Comprehensive multi-disciplinary care standards/guidelines for DMD have been developed by the Centers for Disease Control and Prevention (CDC), and were published in two parts in The Lancet Neurology in 2010. To download the two articles in PDF format, go to the TREAT-NMD website.

1. Physical Therapy

Physical therapists are concerned with enabling patients to reach their maximum physical potential. Their aim is to:

minimize the development of contractures and deformity by developing a programme of stretches and exercises where appropriate anticipate and minimize other secondary complications of a physical nature by recommending bracing and durable medical equipment monitor respiratory function and advise on techniques to assist with breathing exercises and methods of clearing secretions 2. Respiration Assistance Modern "volume ventilators/respirators," which deliver an adjustable volume (amount) of air to the person with each breath, are valuable in the treatment of people with muscular dystrophy related respiratory problems. The ventilator may require an invasive endotracheal or tracheotomy tube through which air is directly delivered, but, for some people non-invasive delivery through a face mask or mouthpiece is sufficient. Positive airway pressure machines, particularly bi-level ones, are sometimes used in this latter way. The respiratory equipment may easily fit on a ventilator tray on the bottom or back of a power wheelchair with an external battery for portability.

Ventilator treatment may start in the mid to late teens when the respiratory muscles can begin to collapse. If the vital capacity has dropped below 40% of normal, a volume ventilator/respirator may be used during sleeping hours, a time when the person is most likely to be under ventilating ("hypoventilating"). Hypoventilation during sleep is determined by a thorough history of sleep disorder with an oximetry study and a capillary blood gas (See Pulmonary Function Testing). A cough assist device can help with excess mucus in lungs by hyperinflation of the lungs with positive air pressure, then negative pressure to get the mucus up. If the vital capacity continues to decline to less than 30 percent of normal, a volume ventilator/respirator may also be needed during the day for more assistance. The person gradually will increase the amount of time using the ventilator/respirator during the day as needed.

F. Prognosis

Duchenne muscular dystrophy is a progressive disease which eventually affects all voluntary muscles and involves the heart and breathing muscles in later stages. The life expectancy is currently estimated to be around 25, but this varies from patient to patient. Recent advancements in medicine are extending the lives of those afflicted. The Muscular Dystrophy Campaign, which is a leading UK charity focusing on all muscle disease, states that "with high standards of medical care young men with Duchenne muscular dystrophy are often living well into their 30s."

In rare cases, persons with DMD have been seen to survive into the forties or early fifties, with the use of proper positioning in wheelchairs and beds, ventilator support (via tracheostomy or mouthpiece), airway clearance, and heart medications, if required. Early planning of the required supports for later-life care has shown greater longevity in people living with DMD.

Curiously, in the mdx mouse model of Duchenne muscular dystrophy, the lack of dystrophin is associated with increased calcium levels and skeletal muscle myonecrosis. The intrinsic laryngeal muscles (ILM) are protected and do not undergo myonecrosis. ILM have a calcium regulation system profile suggestive of a better ability to handle calcium changes in comparison to other muscles, and this may provide a mechanistic insight for their unique pathophysiological properties. The ILM may facilitate the development of novel strategies for the prevention and treatment of muscle wasting in a variety of clinical scenarios.

II. CRISPR SYSTEMS

A. CRISPR and Nucleases

CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced eubacteria genomes and 90% of sequenced archaea. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

Repeats were first described in 1987 for the bacterium Escherichia coli. In 2000, similar clustered repeats were identified in additional bacteria and archaea and were termed Short Regularly Spaced Repeats (SRSR). SRSR were renamed CRISPR in 2002. A set of genes, some encoding putative nuclease or helicase proteins, were found to be associated with CRISPR repeats (the cas, or CRISPR-associated genes).

In 2005, three independent researchers showed that CRISPR spacers showed homology to several phage DNA and extrachromosomal DNA such as plasmids. This was an indication that the CRISPR/cas system could have a role in adaptive immunity in bacteria. Koonin and colleagues proposed that spacers serve as a template for RNA molecules, analogously to eukaryotic cells that use a system called RNA interference.

In 2007 Barrangou, Horvath (food industry scientists at Danisco) and others showed that they could alter the resistance of Streptococcus thermophilus to phage attack with spacer DNA. Doudna and Charpentier had independently been exploring CRISPR-associated proteins to learn how bacteria deploy spacers in their immune defenses. They jointly studied a simpler CRISPR system that relies on a protein called Cas9. They found that bacteria respond to an invading phage by transcribing spacers and palindromic DNA into a long RNA molecule that the cell then uses tracrRNA and Cas9 to cut it into pieces called crRNAs.

CRISPR was first shown to work as a genome engineering/editing tool in human cell culture by 2012 It has since been used in a wide range of organisms including baker's yeast (S. cerevisiae), zebra fish, nematodes (C. elegans), plants, mice, and several other organisms. Additionally CRISPR has been modified to make programmable transcription factors that allow scientists to target and activate or silence specific genes. Libraries of tens of thousands of guide RNAs are now available.

The first evidence that CRISPR can reverse disease symptoms in living animals was demonstrated in March 2014, when MIT researchers cured mice of a rare liver disorder. Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype Ecoli) proteins (called CasA-E in E. coli) form a functional complex, Cascade, that processes CRISPR RNA transcripts into spacer-repeat units that Cascade retains. In other prokaryotes, Cash processes the CRISPR transcripts. Interestingly, CRISPR-based phage inactivation in *E. coli* requires Cascade and Cas3, but not Cas1 and Cas2. The Cmr (Cas RAMP module) proteins found in *Pyrococcus furiosus* and other prokaryotes form a functional complex with small CRISPR RNAs that recognizes and cleaves complementary target RNAs. RNA-guided CRISPR enzymes are classified as type V restriction enzymes.

Cas9 is a nuclease, an enzyme specialized for cutting DNA, with two active cutting sites, one for each strand of the double helix. The team demonstrated that they could disable one or both sites while preserving Cas9's ability to home located its target DNA. Jinek et al. (2012) combined tracrRNA and spacer RNA into a "single-guide RNA" molecule that, mixed with Cas9, could find and cut the correct DNA targets. Jinek et al. (2012) proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of *Francisella novicida* uses a unique, small, CRISPR/Cas-associated RNA (scaRNA) to repress an endogenous transcript encoding a bacterial lipoprotein that is critical for *F. novicida* to dampen host response and promote virulence. Wang et al. (2013) showed that coinjection of Cas9 mRNA and sgRNAs into the germline (zygotes) generated nice with mutations. Delivery of Cas9 DNA sequences also is contemplated.

See also U.S. Patent Publication 2014/0068797, which is incorporated by reference in its entirety.

Clustered Regularly Interspaced Short Palindromic Repeats from *Prevotella* and *Francisella* 1 or CRISPR/Cpf1 is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

CRISPR/Cpf1 was found by searching a published database of bacterial genetic sequences for promising bits of DNA. Its identification through bioinformatics as a CRISPR system protein, its naming, and a hidden Markov model (HMM) for its detection were provided in 2012 in a release of the TIGRFAMs database of protein families. Cpf1 appears in many bacterial species. The ultimate Cpf1 endonuclease that was developed into a tool for genome editing was taken from one of the first 16 species known to harbor it. Two candidate enzymes from *Acidaminococcus* and *Lachnospiraceae* display efficient genome-editing activity in human cells.

A smaller version of Cas9 from the bacterium *Staphylococcus aureus* is a potential alternative to Cpf1.

The systems CRISPR/Cas are separated into three classes. Class 1 uses several Cas proteins together with the CRISPR RNAs (crRNA) to build a functional endonuclease. Class 2 CRISPR systems use a single Cas protein with a crRNA. Cpf1 has been recently identified as a Class II, Type V CRISPR/Cas systems containing a 1,300 amino acid protein.

The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alpha-helical recognition lobe of Cas9.

Cpf1 CRISPR-Cas domain architecture shows that Cpf1 is functionally unique, being classified as Class 2, type V CRISPR system. The Cpf1 loci encode Cas1, Cas2 and Cas4 proteins more similar to types I and III than from type II systems. Database searches suggest the abundance of Cpf1-family proteins in many bacterial species.

Functional Cpf1 doesn't need the tracrRNA, therefore, only crRNA is required. This benefits genome editing because Cpf1 is not only smaller than Cas9, but also it has a smaller sgRNA molecule (proximately half as many nucleotides as Cas9).

The Cpf1-crRNA complex cleaves target DNA or RNA by identification of a protospacer adjacent motif 5'-YTN-3' (where "Y" is a pyrimidine and "N" is any nucleobase) or 5'-TTN-3', in contrast to the G-rich PAM targeted by Cas9. After identification of PAM, Cpf1 introduces a sticky-end-like DNA double-stranded break of 4 or 5 nucleotides overhang.

The CRISPR/Cpf1 system consist of a Cpf1 enzyme and a guide RNA that finds and positions the complex at the correct spot on the double helix to cleave target DNA. CRISPR/Cpf1 systems activity has three stages:

Adaptation, during which Cas1 and Cas2 proteins facilitate the adaptation of small fragments of DNA into the CRISPR array;

Formation of crRNAs: processing of pre-cr-RNAs producing of mature crRNAs to guide the Cas protein; and Interference, in which the Cpf1 is bound to a crRNA to form a binary complex to identify and cleave a target DNA sequence.

B. sgRNA

As an RNA guided protein, Cas9 requires a short RNA to direct the recognition of DNA targets (Mali et al., 2013a). Though Cas9 preferentially interrogates DNA sequences containing a PAM sequence NGG it can bind here without a protospacer target. However, the Cas9-sgRNA complex requires a close match to the sgRNA to create a double strand break (Cho et al., 2013; Hsu et al., 2013). CRISPR sequences in bacteria are expressed in multiple RNAs and then processed to create guide strands for RNA (Bikard et al., 2013). Because Eukaryotic systems lack some of the proteins required to process CRISPR RNAs the synthetic construct sgRNA was created to combine the essential pieces of RNA for Cas9 targeting into a single RNA expressed with the RNA polymerase type III promoter U6 (Mali et al., 2013b,c). Synthetic sgRNAs are slightly over 100 bp at the minimum length and contain a portion which is targets the 20 protospacer nucleotides immediately preceding the PAM sequence NGG; sgRNAs do not contain a PAM sequence.

III. NUCLEIC ACID DELIVERY

As discussed above, in certain embodiments, expression cassettes are employed to express a transcription factor product, either for subsequent purification and delivery to a cell/subject, or for use directly in a genetic-based delivery approach. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promoters such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE A

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen and Baltimore, 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn and Maniatis et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere and Tilghman et al., 1989 |
| t-Globin | Bodine and Ley et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |

TABLE A-continued

Promoter and/or Enhancer

| Promoter/Enhancer | References |
|---|---|
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr and Clarke et al., 1986; Imbra and Karin et al., 1986; Kadesch and Berg, 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla and Siddiqui et al., 1986; Jameel and Siddiqui, 1986; Shaul and Ben-Levy, 1987; Spandau et al., 1988; Vannice et al., 1988 |
| Human Immunodeficiency Virus | Muesing et al., 1987; Hauber and Cullen et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE B

Inducible Elements

| Element | Inducer | References |
|---|---|---|
| MT II | Phorbol Ester (TFA) Heavy metals | Palmiter et al., 1982a, b; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmas et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq and Linzer, 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters. These include the myosin light chain-2 promoter (Franz et al., 1994; Kelly et al., 1995), the muscle creatine kinase enhancer (Jaynes et al., 1988; Horlick et al., 1989; Johnson et al., 1989), the α-actin promoter (Moss et al., 1996), the troponin 1 promoter (Bhaysar et al., 1996); the Na$^+$/Ca$^{2+}$ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1996) and the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. 2A Protease

In some embodiments, a 2A-like self-cleaving domain from the insect virus *Thosea asigna* (TaV 2A peptide) (Chang et al., 2009) is used. These 2A-like domains have been shown to function across eukaryotes and cause cleavage of amino acids to occur co-translationally within the 2A-like peptide domain. Therefore, inclusion of TaV 2A peptide allows the expression of multiple proteins from a single mRNA transcript. Importantly, the domain of TaV when tested in eukaryotic systems have shown greater than 99% cleavage activity (Donnelly et al., 2001).

C. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EP 0273085).

IV. METHODS OF MAKING TRANSGENIC MICE

A particular embodiment of the present invention provides transgenic animals that contain mutations in the dystrophin gene. Also, transgenic animals may express a marker that reflects the production of mutant or normal dystrophin gene product.

In a general aspect, a transgenic animal is produced by the integration of a given construct into the genome in a manner that permits the expression of the transgene using methods discussed above. Methods for producing transgenic animals are generally described by Wagner and Hoppe (U.S. Pat. No. 4,873,191; incorporated herein by reference), and Brinster et al. (1985; incorporated herein by reference).

Typically, the construct is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

RNA for microinjection can be prepared by any means known in the art. For example, RNA for microinjection can be cleaved with enzymes appropriate for removing the bacterial plasmid sequences, and the RNA fragments electrophoresed on 1% agarose gels in TBE buffer, using standard techniques. The RNA bands are visualized by staining with ethidium bromide, and the band containing the expression sequences is excised. The excised band is then placed in dialysis bags containing 0.3 M sodium acetate, pH 7.0. RNA is electroeluted into the dialysis bags, extracted with a 1:1 phenol:chloroform solution and precipitated by two volumes of ethanol. The RNA is redissolved in 1 ml of low salt buffer (0.2 M NaCl, 20 mM Tris, pH 7.4, and 1 mM EDTA) and purified on an Elutip-D® column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind RNA to the column matrix. After one wash with 3 ml of low salt buffer, the RNA is eluted with 0.4 ml high salt buffer and precipitated by two volumes of ethanol. RNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of RNA for microinjection are described in in Palmiter et al. (1982a,b); and in Sambrook and Russell (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

V. PHARMACEUTICAL COMPOSITIONS AND DELIVERY METHODS

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs, proteins or delivery vectors stable and allow for uptake by target cells. Aqueous compositions of the present invention comprise an effective amount of the drug, vector or proteins, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route, but generally including systemic administration. This includes oral, nasal, or buccal. Alternatively, administration may be by intradermal, subcutaneous, intramuscular, intraperitoneal or intravenous injection, or by direct injection into muscle tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VI. SEQUENCE TABLES

TABLE 1

Sequence of primers for sgRNA targeting DMD and Dmd exon 45 splicing acceptor site

| ID | Sequence (5'-3') | SEQ ID NO. |
|---|---|---|
| Ex45-gRNA#3-Top | CACCGCGCTGCCCAATGCCATCCTG | 1 |
| Ex45-gRNA#3-Bot | AAACCAGGATGGCATTGGGCAGCGC | 2 |
| Ex45-gRNA#4-Top | CACCGCTTACAGGAACTCCAGGA | 3 |
| Ex45-gRNA#4-Bot | AAACTCCTGGAGTTCCTGTAAGC | 4 |
| Ex45-gRNA#5-Top | CACCGAGGAACTCCAGGATGGCATT | 5 |
| Ex45-gRNA#5-Bot | AAACAATGCCATCCTGGAGTTCCTC | 6 |
| Ex45-gRNA#6-Top | CACCGCGCTGCCCAATGCCATCC | 7 |
| Ex45-gRNA#6-Bot | AAACGGATGGCATTGGGCAGCGC | 8 |
| mDmd-T7E1-Ex45-F | CTAACATAAAAGGTGTCTTTCTATC | 9 |

TABLE 1-continued

Sequence of primers for sgRNA targeting DMD and Dmd exon 45 splicing acceptor site

| ID | Sequence (5'-3') | SEQ ID NO. |
|---|---|---|
| mDmd-T7E1-Ex45-R | GGCAATCCCTCATGATTTTTAGCAC | 10 |
| DMD-T7E1-Ex45-F | GTCTTTCTGTCTTGTATCCTTTGG | 11 |
| DMD-T7E1-Ex45-R | AATGTTAGTGCCTTTCACCC | 12 |

TABLE 2

Sequence of primers for sgRNA targeting Dmd exon 44 to generate the mouse model

| ID | Mouse Model | Sequence (5'-3') | SEQ ID NO. |
|---|---|---|---|
| mDmd-In44-2-Top | Δex44 | CACCGGTAGTTCTGAATCAGGAGGA | 13 |
| mDmd-In44-2-Bot | Δex44 | AAACTCCTCCTGATTCAGAACTACC | 14 |
| mDmd-In44-6-Top | Δex44 | CACCGTATGTTGGAACCAGTCCAGA | 15 |
| mDmd-In44-6-Bot | Δex44 | AAACTCTGGACTGGTTCCAACATAC | 16 |

TABLE 3

Sequence of primers for in vitro transcription of sgRNA

| ID | Mouse Model | Sequence (5'-3') | SEQ ID NO. |
|---|---|---|---|
| exon 44_T7-In44-2-F | Δex44 | GAATTGTAATACGACTCACTATAGGG GTAGTTCTGAATCAGGAGGA | 17 |
| exon 44_T7-In44-6-F | Δex44 | GAATTGTAATACGACTCACTATAGGG TATGTTGGAACCAGTCCAGA | 18 |
| exon 44_T7-Rv | Δex44 | AAAAGCACCGACTCGGTGCCAC | 19 |

TABLE 4

Sequence of primers for genotyping

| ID | Mouse Model | Sequence (5'-3') | SEQ ID NO. |
|---|---|---|---|
| Geno44-F | Δex44 | GCTGAGGGGGAGACAGTAGA | 20 |
| Geno44-R | Δex44 | TCAGAAGGCATTTTGTCAAT | 21 |

TABLE 5 gRNA genomic target sequences

| sgRNA ID | Sequence (5'-3') | SEQ ID NO. |
|---|---|---|
| Ex45-gRNA#3 | CGCTGCCCAATGCCATCCTG | 39 |
| Ex45-gRNA#4 | ATCTTACAGGAACTCCAGGA | 40 |
| Ex45-gRNA#5 | AGGAACTCCAGGATGGCATT | 41 |
| Ex45-gRNA#6 | CGCTGCCCAATGCCATCC | 42 |

TABLE 5-continued gRNA genomic target sequences

| sgRNA ID | Sequence (5'-3') | SEQ ID NO. |
|---|---|---|
| Ex43-gRNA#1 | GTTTTAAAATTTTTATATTA | 43 |
| Ex43-gRNA#2 | TTTTATATTACAGAATATAA | 44 |
| Ex43-gRNA#4 | TATGTGTTACCTACCCTTGT | 45 |
| Ex43-gRNA#6 | GTACAAGGACCGACAAGGGT | 46 |

TABLE 6 gRNA sequences

| sgRNA ID | Sequence (5'-3') | SEQ ID NO. |
|---|---|---|
| Ex45-gRNA#3 | CAGGAUGGCAUUGGGCAGCG | 47 |
| Ex45-gRNA#4 | UCCUGGAGUUCCUGUAAGAU | 48 |
| Ex45-gRNA#5 | AAUGCCAUCCUGGAGUUCCU | 49 |
| Ex45-gRNA#6 | GGAUGGCAUUGGGCAGCG | 50 |
| Ex43-gRNA#1 | UAAUAUAAAAAUUUUAAAAC | 51 |
| Ex43-gRNA#2 | UUAUAUUCUGUAAUAUAAAA | 52 |
| Ex43-gRNA#4 | ACAAGGGUAGGUAACACAUA | 53 |
| Ex43-gRNA#6 | ACCCUUGUCGGUCCUUGUAC | 54 |

VII. EXAMPLES

The following examples are included to demonstrate preferred embodiments of the disclosure. It should be appreciated by those of skill in the art that the techniques disclosed in the examples which follow represent techniques which function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Study Approval.

All experimental procedures involving animals in this study were reviewed and approved by the University of Texas Southwestern Medical Center's Institutional Animal Care and Use Committee.

Plasmids.

The pSpCas9(BB)-2A-GFP (PX458) plasmid containing the human codon optimized SpCas9 gene with 2A-EGFP and the backbone of sgRNA was purchased from Addgene (Plasmid #48138). Cloning of sgRNA was done using Bbs I sites. The AAV TRISPR-CK8-GFP plasmid containing three sgRNAs driven by U6, H1 or 7SK promoter and GFP driven by CK8 promoter.

Human iPSCs Maintenance and Nucleofection.

Human iPSCs were cultured in mTeSR™ 1 media (STEMCELL Technologies) and passaged approximately every 4 days (1:18 split ratio). One hour before nucleofection, iPSCs were treated with 10 µM ROCK inhibitor (Y-27632) and dissociated into single cells using Accutase (Innovative Cell Technologies, Inc.). $1 \times 10^6$ iPS cells were mixed with 5 µg of pLbCpf1-2A-GFP or pAsCpf1-2A-GFP plasmid and nucleofected using the P3 Primary Cell 4D-Nucleofector X kit (Lonza) according to manufacturer's protocol. After nucleofection, iPSCs were cultured in mTeSR™ 1 media supplemented with 10 µM ROCK inhibitor, penicillin-streptomycin (1:100) (ThermoFisher Scientific) and 100 µg/ml Primosin (InvivoGen). Three days post-nucleofection, GFP(+) and (−) cells were sorted by FACS and subjected to T7E1 assay. Single clones derived from GFP(+) iPSCs were picked and sequenced.

Genomic DNA Isolation.

Genomic DNA of mouse 10T½ fibroblasts, mouse C2C12, human 293 and human iPSCs was isolated using DirectPCR (cell) lysis reagent (VIAGEN) according to manufacturer's protocol.

PCR Amplification of Genomic DNA.

Genomic DNA was PCR-amplified using GoTaq DNA polymerase (Promega) with primers. PCR products were gel purified and subcloned into pCRII-TOPO vector (Invitrogen) according to the manufacturer's protocol. Individual clones were picked and the DNA was sequenced. Primer sequences are listed in supplemental material.

T7E1 Analysis of PCR Products.

Mismatched duplex DNA was obtained by denaturing/renaturing of 25 µl of the genomic PCR product using the following conditions: 95° C. for 5 mins, 95° C. to 85° C. (−2.0° C./seconds), 85° C. to 25° C. (−0.1° C./seconds), hold at 4° C. Then 25 µl of the mismatched duplex DNA was incubated with 2.7 µl of 10×NEB buffer 2 and 0.3 µl of T7E1 (New England BioLabs) at 37° C. for 90 minutes. The T7E1 digested PCR product was analyzed by 2% agarose gel electrophoresis.

Human Cardiomyocyte Differentiation.

Human iPSCs were cultured in mTeSR™1 media for 3 days until they reached 90% confluence. To differentiate the iPSCs to cardiomyocytes, the iPSCs were cultured in CDM3-C media for 2 days, followed by CDM3-59 media for 2 days, followed by CDM3 media for 6 days, followed by selective media for 10 days and lastly by basal media for 2 days. Then, the cardiomyocytes were dissociated using TrypLE media and re-plated at $2 \times 10^6$ per well in a 6-well dish. Differentiation medium recipe can be found in supplemental materials.

Dystrophin Western Blot Analysis.

After 30 days post-differentiation, $2 \times 10^6$ cardiomyocytes were harvested and lysed with lysis buffer (10% SDS, 62.5 mM Tris pH=6.8, 1 mM EDTA, and protease inhibitor). Cell lysates were passed through a 22G syringe and then a 27G syringe, 10 times each. Protein concentration was determined by BCA assay and 50 ug of total protein was loaded onto an acrylamide gel. After running at 100V (20 mA) for 5 hours and followed by 1 hour 20 min transfer to PVDF membrane at 35V (200 mA) at 4° C. The blot was incubated with mouse anti-dystrophin antibody (MANDYS8, Sigma-Aldrich, D8168) at 4° C. overnight and with goat anti-mouse HRP antibody (Bio-Rad Laboratories) at RT for 1 hour. The blot was developed using Western Blotting Luminol Reagent (Santa Cruz, sc-2048). The loading control was determined by blotting with mouse anti-vinculin antibody (Sigma-Aldrich, V9131).

CRISPR/Cas9-Mediated Exon 44 Deletion in Mice.

Two single-guide RNA (sgRNA) specific intronic regions surrounding exon 44 sequence of the mouse Dmd locus were cloned into vector PX458 using the primers from Table 1.

For the in vitro transcription of sgRNA, T7 promoter sequence was added to the sgRNA template by PCR using the primers from Table 2. The gel purified PCR products were used as template for in vitro transcription using the MEGAshortscript T7 Kit (Life Technologies). sgRNA were purified by MEGAclear kit (Life Technologies) and eluted with nuclease-free water (Ambion). The concentration of guide RNA was measured by a NanoDrop instrument (Thermo Scientific).

Genotyping of ΔEx44 Mice.

ΔEx44 mice were genotyped using primers encompassing the targeted region from Table 3. Tail biopsies were digested in 100 μL of 25 mM NaOH, 0.2 mM EDTA (pH 12) for 20 min at 95° C. Tails were briefly centrifuged followed by addition of 100 μL of 40 mM Tris-HCl (pH 5) and mixed to homogenize. Two microliters of this reaction was used for subsequent PCR reactions with the primers below, followed by gel electrophoresis.

Histological Analysis of Muscles.

Skeletal muscles from WT and ΔEx44 mice were individually dissected and cryoembedded in a 1:2 volume mixture of Gum Tragacanth powder (Sigma-Aldrich) to Tissue Freezing Medium (TFM) (Triangle Bioscience). All embeds were snap frozen in isopentane heat extractant supercooled to −155° C. Resulting blocks were stored overnight at −80° C. prior to sectioning. Eight-micron transverse sections of skeletal muscle, and frontal sections of heart were prepared on a Leica CM3050 cryostat and air-dried prior to same day staining. H&E staining was performed according to established staining protocols and dystrophin immunohistochemistry was performed using MANDYS8 monoclonal antibody (Sigma-Aldrich) with modifications to manufacturer's instructions. In brief, cryostat sections were thawed and rehydrated/delipidated in 1% triton/phosphate-buffered-saline, pH 7.4 (PBS). Following delipidation, sections were washed free of Triton, incubated with mouse IgG blocking reagent (M.O.M. Kit, Vector Laboratories), washed, and sequentially equilibrated with MOM protein concentrate/PBS, and MANDYS8 diluted 1:1800 in MOM protein concentrate/PBS. Following overnight primary antibody incubation at 4° C., sections were washed, incubated with MOM biotinylated anti-mouse IgG, washed, and detection completed with incubation of Vector fluorescein-avidin DCS. Nuclei were counterstained with propidium iodide (Molecular Probes) prior to cover slipping with Vectashield.

Example 2—Results

Exon 44 Deleted DMD Patient iPSC-Derived Cardiomyocytes Express Dystrophin after CRISPR Cas9 Mediated Genome Editing by Exon Skipping.

A common hot spot mutation region in DMD patients is the deletion of exon 44, which leads to skipping of exon 45 in approximately ~12% of DMD patients. The DMD patient PBMC-derived iPSCs (TX11) used in this study have an exon 44 deletion, which introduces a premature termination codon within exon 45 and subsequently disrupts the open reading frame (ORF) of the DMD gene. To restore the ORF of the TX11 DMD patient iPSCs, a single guide RNA was used to disrupt the splicing acceptor of exon 45, which results in splicing of exons 43 to 46 and restoration of the protein reading frame (FIGS. 1A, 3A). The sequence of the intron 44 and exon 45 junction contains a 33 base pair conserved region in mouse and human genomes (FIGS. 1B, 3B). To test sgRNA efficiency within this region, sgRNAs were designed to target the splicing junction sites of exon 43 and 45 (FIGS. 1B, 3C, 3D). The cleavage efficiency of these gRNAs was validated in both mouse 10T½ cells and human 293 cells. By T7E1 assay, it was demonstrated that 4 sgRNAs (G3, G4, G5 and G6) efficiently cause DNA cleavage at DMD exon 43 or 45 locus (FIGS. 1C, 3E, 3F; Tables 5, 6).

The sgRNA3 (G3) was then tested on TX11 DMD patient iPSCs and observed genome cleavage at DMD exon 45 locus by T7E1 assay (FIG. 1D). 48 single clones were picked from a pool of edited TX11 iPSCs mixture and sequenced the edited genomic region. Out of 48 clones, two clones with an abolished splicing acceptor site were observed, which should restore the DMD ORF (FIG. 1E). Exon 45 skipped TX11 iPSC single clones were differentiated using a previously described method (see Materials and Methods section). Restoration of dystrophin protein expression in the clones was confirmed by Western blot analysis (FIG. 1F). To further assess the efficiency of the sgRNAs in vivo, exon 45 sgRNA3 (G3) and sgRNA4 (G4) were then cloned into AAV9-TRISPR-CK8 plasmid (FIG. 1G). Efficiency of the two sgRNAs was evaluated in mouse C2C12 cells, the genome cleavage was observed at DMD exon 45 locus by T7E1 assay (FIG. 1H).

Exon 44 Deleted DMD Patient iPSC-Derived Cardiomyocytes Express Dystrophin after CRISPR/Cas9 Mediated Genome Editing by Exon Skipping.

iPSCs from DMD patients (TX11 and TX12) that have deletion of exon 44 were then generated by reprogramming PBMCs derived from the patients (FIGS. 4A, 4B). Exon 45 sgRNA3 (G3) was tested on TX11 DMD patient iPSCs and 48 single clones were picked from a pool of edited TX11 iPSCs mixture. The clones were then differentiated using a previously described method (see Materials and Methods section). Restoration of dystrophin protein expression in the clones was confirmed by Western blot analysis (FIG. 1F). The edited genomic region was sequenced. Out of 48 clones, two clones with an abolished splicing acceptor site were observed, which should restore the DMD ORF (FIG. 1E). Exon 43 sgRNA4 (E43G4), exon 43 sgRNA6 (E43g6) and exon 45 sgRNA4 (E45g4) was then tested on TX11 DMD patient iPSCs. The restoration of dystrophin in these TX11 DMD patient iPSCs was confirmed by Western blot analysis and immunostaining (FIGS. 4C, 4D).

Humanized DMD ΔEx44 Mouse Model Recapitulates Muscle Dystrophy Phenotype.

To investigate CRISPR/Cas9-mediated exon 45 skipping in vivo, a mimic of the human "hot spot" region was generated in a mouse model by deleting the exon 44 using CRISPR/Cas9 system directed by 2 single guide RNAs (sgRNA) (FIGS. 2A, 5A). sgRNAs targeting 5' end (In44-1, In44-2 or In44-3) and 3' end (In44-4, In44-5, In44-6) of Dmd exon 44 were designed and validated (Tables 5, 6). A T7E1 assay showed different CRISPR/Cas9 cleavage efficiencies at Dmd intron 44 in 10T½ mouse fibroblasts (FIG. 2B). C57BL/6 zygotes were co-injected with in vitro transcribed Cas9 mRNA and in vitro transcribed In44-2 and In44-6 sgRNA and re-implanted into pseudo-pregnant females.

The deletion of Dmd exon 44 was confirmed by DNA genotyping (FIG. 2C). The deletion of exon 44 placed the dystrophin gene out of frame leading to the absence of dystrophin protein in skeletal muscle and heart (FIGS. 2E and 2F). Mice lacking exon 44 showed pronounced dystrophic muscle changes by 1-month of age (FIG. 2G). Mice lacking exon 44 showed decreased muscle function (FIGS. 5C, 5D, 5E). Serum analysis of ΔEx44 mice showed a significant increase of creatine kinase (CK) activity, which is a sign of muscle damage (FIGS. 2D, 5B). Taken together, dystrophin protein expression, muscle histology and serum creatine kinase activity, and muscle function validated dystrophic phenotype of ΔEx44 mouse model.

Correction of DMD Exon 44 Deletion in Mice by Intramuscular AAV9 Delivery of Gene Editing Components.

To further assess the efficiency of the sgRNAs in vivo, exon 45 sgRNA3 (G3) and sgRNA4 (G4) were then cloned into AAV9-TRISPR-CK8 plasmid (FIG. 1G). Efficiency of the two sgRNAs was evaluated in mouse C2C12 cells, the genome cleavage was observed at DMD exon 45 locus by T7E1 assay (FIG. 1H). The AAV9-Cas9 and AAV9-exon 45-sgRNA4 were then injected into the TA muscle of Δ44 DMD mice. 3 weeks after intramuscular injection, restoration of dystrophin protein expression in the TA muscle of Δ44 DMD mice was confirmed by immunostaining (FIG. 6A), histology (FIG. 6B), and Western blot analysis (FIG. 6C). The genome cleavage of exon 45 locus in the corrected Δ44 DMD mice was validated in a T7E1 assay (FIG. 6D). RT-PCR analysis of the TA muscles from WT, Δ44 and Δ44 mice 3 weeks after intramuscular injection of AAV9-Cas9/exon45-sgRNA4 confirmed skipping of exon 45 (FIG. 6E). RT-PCR sequence analysis of TOPO-TA (topoisomerase-based thymidine to adenosine) generated clones revealed both exon skipping of exon 45 and reframing of exon 45 contributed to the restoration of dystrophin open reading frame (FIGS. 6F, 6G).

Systemic AAV9 Delivery of Gene Editing Components to Δ44 Mice Rescues Dystrophin Expression.

Rescue of the disease phenotype was then tested by intraperitoneal injection of AAV9-Cas9 and AAV9-exon45-sgRNA4 into Δ44 mice, which allowed for systemic distribution of the AAV9 vectors. 4 weeks after systemic delivery, the restoration of dystrophin protein expression in the TA, diaphragm, triceps, and cardiac muscles of Δ44 DMD mice was confirmed by Western blot analysis (FIG. 7A), histology, and immunostaining (FIG. 7B). An optimized sgRNA to Cas9 ratio was confirmed by improved correction efficiency in the Δ44 DMD mice. Serum creatine kinase level was decreased in the corrected Δ44 DMD mice (FIG. 7C).

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference.

Amoasii et al., *Sci Transl Med.* 9(418), 2017.
Angel et al., *Mol. Cell. Biol.*, 7:2256, 1987a.
Angel et al., *Cell*, 49:729, 1987b.
Baichwal and Sugden, In: *Gene Transfer*, Kucherlapati (Ed), NY, Plenum Press, 117-148, 1986.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-7, 1997.
Benvenisty and Neshif, *Proc. Natl. Acad. Sci. USA*, 83:9551-9555, 1986.
Berkhout et al., *Cell*, 59:273-282, 1989.
Bhaysar et al., *Genomics*, 35(1):11-23, 1996.
Bikard et al., *Nucleic Acids Res.* 41(15): 7429-7437, 2013.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brinster et al., *Proc. Natl. Acad. Sci. USA*, 82(13):4438-4442, 1985.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Celander and Haseltine, *J. Virology*, 61:269, 1987.
Celander et al., *J. Virology*, 62:1314, 1988.
Chandler et al., Cell, 33:489, 1983.
Chang et al., *Mol. Cell. Biol.*, 9:2153, 1989.
Chang et al., *Stem Cells.*, 27:1042-1049, 2009.
Chatterjee et al., *Proc. Natl. Acad. Sci. USA*, 86:9114, 1989.
Chen and Okayama, *Mol. Cell Biol.*, 7:2745-2752, 1987.
Cho et al., *Nat. Biotechnol.* 31(3): 230-232, 2013.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Donnelly et al., *J. Gen. Virol.* 82, 1027-1041, 2001.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
EP 0273085
Fechheimer et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak et al., *Mol. Cell. Biol.*, 6:3667, 1986.
Foecking et al., *Gene*, 45(1):101-105, 1986.
Fraley et al., *Proc Natl. Acad. Sci. USA*, 76:3348-3352, 1979
Franz et al., *Cardoscience*, 5(4):235-43, 1994.
Friedmann, *Science*, 244:1275-1281, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.

Gopal-Srivastava et al., *J. Mol. Cell. Biol.*, 15(12):7081-90, 1995.
Graham and Prevec, In: *Methods in Molecular Biology: Gene Transfer and Expression Protocol*, Murray (Ed.), Humana Press, Clifton, N.J., 7:109-128, 1991.
Graham and van der Eb, *Virology*, 52:456-467, 1973.
Graham et al., *J. Gen. Virol.*, 36:59-72, 1977.
Greene et al., *Immunology Today*, 10:272, 1989
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Nat'l. Acad. Sci. USA* 90:2812-2816, 1993.
Hirochika et al., *J. Virol.*, 61:2599, 1987.
Holbrook et al., *Virology*, 157:211, 1987.
Horlick and Benfield, *Mol. Cell. Biol.*, 9:2396, 1989.
Horwich et al., *J Virol.*, 64:642-650, 1990.
Hsu et al., *Natl Biotechnol.* 31:827-832, 2013
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jinek et al., *Science* 337, 816-821, 2012.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al., *J. Biol. Chem.*, 266(6):3361-3364, 1991.
Kawamoto et al., *Mol. Cell. Biol.*, 8:267, 1988.
Kelly et al., *J. Cell Biol.*, 129(2):383-96, 1995.
Kiledjian et al., *Mol. Cell. Biol.*, 8:145, 1988.
Kimura et al., *Dev. Growth Differ.*, 39(3):257-65, 1997.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, N Y, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
LaPointe et al., *Hypertension*, 27(3):715-22, 1996
LaPointe et al., *J Biol. Chem.*, 263(19):9075-8, 1988.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Nature*, 294:228, 1981.
Levinson et al., *Nature*, 295:79, 1982.
Levrero et al., *Gene*, 101:195-202, 1991.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors and Varmus, *Proc. Natl. Acad. Sci. USA*, 80:5866, 1983.
Mali et al., *Science* 339, 823-826, 2013a.
Mali et al., *Nat Methods* 10, 957-963, 2013b.
Mali et al., *Nat. Biotechnol.* 31:833-838, 2013c.
Mann et al., *Cell*, 33:153-159, 1983.
Markowitz et al., *J. Virol.*, 62:1120-1124, 1988.
McNeall et al., *Gene*, 76:81, 1989.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Moss et al., *J. Gen. Physiol.*, 108(6):473-84, 1996.
Muesing et al., *Cell*, 48:691, 1987.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ondek et al., *EMBO J.*, 6:1017, 1987.
Ornitz et al., *Mol. Cell. Biol.*, 7:3466, 1987.
Palmiter et al., *Cell*, 29:701, 1982a.
Palmiter et al., *Nature*, 300:611, 1982b.
Paskind et al., *Virology*, 67:242-248, 1975.
Pech et al., *Mol. Cell. Biol.*, 9:396, 1989.
Perales et al., *Proc. Natl. Acad. Sci. USA*, 91(9):4086-4090, 1994.
Perez-Stable and Constantini, *Mol. Cell. Biol.*, 10:1116, 1990.
Picard et al., *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotech. Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A survey of molecular cloning vectors and their uses*, Stoneham: Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Natl. Acad. Sci. USA*, 86:9079-9083, 1989.
Sambrook and Russell, *Molecular Cloning: A Laboratory Manual* 3$^{rd}$ Ed., Cold Spring Harbor Laboratory Press, 2001.
Sakai et al., *Genes and Dev.*, 2:1144, 1988.

Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp et al., *Cell*, 59:229, 1989.
Shaul and Ben-Levy, *EMBO J.*, 6:1913, 1987.
Sherman et al., *Mol. Cell. Biol.*, 9:50, 1989.
Sleigh et al., *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, *In: Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Top et al., *J. Infect. Dis.*, 124:155-160, 1971.
Tronche et al., *Mol. Biol. Med.*, 7:173, 1990.
Trudel and Constantini, *Genes and Dev.* 6:954, 1987.
Tur-Kaspa et al., *Mol. Cell Biol.*, 6:716-718, 1986.
Tyndell et al., *Nuc. Acids. Res.*, 9:6231, 1981.
Vannice and Levinson, *J. Virology*, 62:1305, 1988.
Varmus et al., *Cell*, 25:23-36, 1981.
Vasseur et al., *Proc Natl. Acad. Sci. U.S.A.*, 77:1068, 1980.
Wagner et al., *Proc. Natl. Acad. Sci. USA*, 87(9):3410-3414, 1990.
Wang and Calame, *Cell*, 47:241, 1986.
Wang et al., *Cell*, 153:910-910, 2013.
Weber et al., *Cell*, 36:983, 1984.
Weinberger et al. *Mol. Cell. Biol.*, 8:988, 1984.
Winoto et al., *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu et al., *Cell Stem Cell* 13, 659-662, 2013.
Wu et al., *Nat Biotechnol* 32, 670-676, 2014.
Yamauchi-Takihara et al., *Proc. Natl. Acad. Sci. USA*, 86(10):3504-3508, 1989.
Yang et al., *Proc. Natl. Acad. Sci. USA*, 87:9568-9572, 1990.
Yutzey et al. *Mol. Cell. Biol.*, 9:1397, 1989.
Zelenin et al., *FEBS Lett.*, 280:94-96, 1991.
Ziober and Kramer, *J. Bio. Chem.*, 271(37):22915-22922, 1996.

---

What is claimed:

1. A mouse whose genome comprises a deletion of exon 44 of the endogenous dystrophin gene resulting in an out of frame shift and a premature stop codon in exon 45; wherein the mouse is homozygous for the deletion; and wherein the mouse does not exhibit detectable dystrophin protein in heart or skeletal muscle.

2. The mouse of claim 1, wherein the mouse exhibits increased serum creatine kinase levels.

3. An isolated cell obtained from the mouse of claim 1.

4. A mouse produced by a method comprising the steps of:
   (a) contacting a fertilized oocyte with a nucleotide sequence encoding Cpf1 or Cas9 and two single guide RNAs (sgRNAs) targeting sequences flanking exon 44 of the mouse dystrophin gene, thereby creating a modified oocyte, wherein deletion of exon 44 by Cpf1 or Cas9 results in an out of frame shift and a premature stop codon in exon 45; and
   (b) transferring the modified oocyte into a recipient female;
wherein the mouse is homozygous for the deletion; and wherein the mouse does not exhibit detectable dystrophin protein in heart or skeletal muscle.

5. The mouse of claim 4, wherein the two sgRNAs comprise SEQ ID NOs: 1 and 2, 3 and 4, 5 and 6, 7 and 8, 27 and 28, 29 and 30, 31 and 32, 33 and 34, 35 and 36, or 37 and 38.

6. The mouse of claim 4, wherein the Cas9 is provided as naked plasmid DNA or chemically-modified mRNA.

* * * * *

SEQUENCE LISTING

```
<160> NUMBER OF SEQ ID NOS: 67

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caccgcgctg cccaatgcca tcctg                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaccaggat ggcattgggc agcgc                                           25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caccgcttac aggaactcca gga                                             23

<210> SEQ ID NO 4
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaactcctgg agttcctgta agc                                              23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccgaggaa ctccaggatg gcatt                                            25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaacaatgcc atcctggagt tcctc                                            25

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caccgcgctg cccaatgcca tcc                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaacggatgg cattgggcag cgc                                              23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctaacataaa aggtgtcttt ctatc                                            25

<210> SEQ ID NO 10
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcaatccct catgattttt agcac                                          25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtctttctgt cttgtatcct ttgg                                           24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatgttagtg cctttcaccc                                                20

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
caccggtagt tctgaatcag gagga                                          25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaactcctcc tgattcagaa ctacc                                          25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccgtatgt tggaaccagt ccaga                                          25

<210> SEQ ID NO 16
<211> LENGTH: 25
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 16
aaactctgga ctggttccaa catac        25

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gaattgtaat acgactcact atagggtag ttctgaatca ggagga        46

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gaattgtaat acgactcact atagggtatg ttggaaccag tccaga        46

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aaaagcaccg actcggtgcc ac        22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gctgaggggg agacagtaga        20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
tcagaaggca ttttgtcaat        20

<210> SEQ ID NO 22
<211> LENGTH: 53
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 22
ttttgccttt tggtatcttt acaggaactc caggatggca ttgggcagcg gca    53

<210> SEQ ID NO 23
<211> LENGTH: 53
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 23
tgccgctgcc caatgccatc ctggagttcc tgtaagatac caaaaaggca aaa    53

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 24
cttacaggaa ctccaggatg gcattgggca gcggc    35

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (28)..(28)
<223> OTHER INFORMATION: a, c, t, g, unknown or other

<400> SEQUENCE: 25 cattttgtt ttgccttttt ggtattgngc agcggc    36

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 26
ggtatcttac tggcattggg cagcggc    27

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 27
caccggctta caggaactcc agga    24

<210> SEQ ID NO 28

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaactcctgg agttcctgta agcc                                          24

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
caccgatctt acaggaactc cagga                                         25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aaactcctgg agttcctgta agatc                                         25

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caccgtttta aaatttttat atta                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
aaactaatat aaaaatttta aaac                                          24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caccgtttta tattacagaa tataa                                         25

<210> SEQ ID NO 34
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aaacttatat tctgtaatat aaaac                                           25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caccgtatgt gttacctacc cttgt                                           25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaacacaagg gtaggtaaca catac                                           25

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
caccgtacaa ggaccgacaa gggt                                            24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aaacaccctt gtcggtcctt gtac                                            24

<210> SEQ ID NO 39
<211> LENGTH: 20
<212> TYPE: DNA
<213> ORGANISM: Mus sp.

<400> SEQUENCE: 39
cgctgcccaa tgccatcctg                                                 20

<210> SEQ ID NO 40
<211> LENGTH: 20
<212> TYPE: DNA
<213> ORGANISM: Mus sp.

<400> SEQUENCE: 40
```

```
atcttacagg aactccagga                                              20

<210> SEQ ID NO 41
<211> LENGTH: 20
<212> TYPE: DNA
<213> ORGANISM: Mus sp.

<400> SEQUENCE: 41
aggaactcca ggatggcatt                                              20

<210> SEQ ID NO 42
<211> LENGTH: 18
<212> TYPE: DNA
<213> ORGANISM: Mus sp.

<400> SEQUENCE: 42
cgctgcccaa tgccatcc                                                18

<210> SEQ ID NO 43
<211> LENGTH: 20
<212> TYPE: DNA
<213> ORGANISM: Mus sp.

<400> SEQUENCE: 43
gttttaaaat ttttatatta                                              20

<210> SEQ ID NO 44
<211> LENGTH: 20
<212> TYPE: DNA
<213> ORGANISM: Mus sp.

<400> SEQUENCE: 44
ttttatatta cagaatataa                                              20

<210> SEQ ID NO 45
<211> LENGTH: 20
<212> TYPE: DNA
<213> ORGANISM: Mus sp.

<400> SEQUENCE: 45
tatgtgttac ctacccttgt                                              20

<210> SEQ ID NO 46
<211> LENGTH: 20
<212> TYPE: DNA
<213> ORGANISM: Mus sp.

<400> SEQUENCE: 46
gtacaaggac cgacaagggt                                              20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
caggauggca uugggcagcg                                              20

<210> SEQ ID NO 48
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uccuggaguu ccuguaagau                                              20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aaugccaucc uggaguuccu                                              20

<210> SEQ ID NO 50
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ggauggcauu gggcagcg                                                18

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaauauaaaa auuuuaaaac                                              20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uuauauucug uaauauaaaa                                              20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
acaaggguag guaacacaua                                              20

<210> SEQ ID NO 54
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 54
acccuugucg guccuuguac                                                     20

<210> SEQ ID NO 55
<211> LENGTH: 40
<212> TYPE: DNA
<213> ORGANISM: Homo sapiens

<400> SEQUENCE: 55
tatcttacag gaactccagg atggcattgg gcagcggcaa                               40

<210> SEQ ID NO 56
<211> LENGTH: 40
<212> TYPE: DNA
<213> ORGANISM: Mus sp.

<400> SEQUENCE: 56
tggcttacag gaactccagg atggcattgg gcagcgtcaa                               40

<210> SEQ ID NO 57
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tttggtatct tacaggaact ccaggatggc attgggcagc ggca                         44

<210> SEQ ID NO 58
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ctgttttaaa atttttatat tacagaatat aaaagatagt ctacaacaaa gctca             55

<210> SEQ ID NO 59
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tgggaaaaag ttaacaaaat gtacaaggac cgacaagggt aggtaacaca tata              54

<210> SEQ ID NO 60
<211> LENGTH: 72
<212> TYPE: DNA
<213> ORGANISM: Mus sp.
<220> FEATURE:
<221> NAME/KEY: CDS
<222> LOCATION: (1)..(72)

<400> SEQUENCE: 60
```

```
gct aaa tac aaa tgg tat ctt aag gaa ctc cag gat ggc att ggg cag    48
Ala Lys Tyr Lys Trp Tyr Leu Lys Glu Leu Gln Asp Gly Ile Gly Gln
1               5                   10                  15 cgt caa gct gtt gtc aga aca ctg                                    72
Arg Gln Ala Val Val Arg Thr Leu
            20
```

```
<210> SEQ ID NO 61
<211> LENGTH: 24
<212> TYPE: PRT
<213> ORGANISM: Mus sp.

<400> SEQUENCE: 61

Ala Lys Tyr Lys Trp Tyr Leu Lys Glu Leu Gln Asp Gly Ile Gly Gln
1               5                   10                  15

Arg Gln Ala Val Val Arg Thr Leu
            20

<210> SEQ ID NO 62
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(69)

<400> SEQUENCE: 62
```

```
aga atg tac aag gaa cga caa ggg aac tcc agg atg gca ttg ggc agc    48
Arg Met Tyr Lys Glu Arg Gln Gly Asn Ser Arg Met Ala Leu Gly Ser
1               5                   10                  15 gtc aag ctg ttg tca gaa cac tga                                    72
Val Lys Leu Leu Ser Glu His
            20
```

```
<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Met Tyr Lys Glu Arg Gln Gly Asn Ser Arg Met Ala Leu Gly Ser
1               5                   10                  15

Val Lys Leu Leu Ser Glu His
            20

<210> SEQ ID NO 64
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(72)

<400> SEQUENCE: 64
```

```
aga atg tac aag gaa cga caa ggg aac tcc aag gat ggc att ggg cag    48
Arg Met Tyr Lys Glu Arg Gln Gly Asn Ser Lys Asp Gly Ile Gly Gln
1               5                   10                  15
```

```
cgt caa gct gtt gtc aga aca ctg                                         72
Arg Gln Ala Val Val Arg Thr Leu
            20

<210> SEQ ID NO 65
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Met Tyr Lys Glu Arg Gln Gly Asn Ser Lys Asp Gly Ile Gly Gln
1               5                   10                  15

Arg Gln Ala Val Val Arg Thr Leu
            20

<210> SEQ ID NO 66
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(72)

<400> SEQUENCE: 66 aga atg tac aag gaa cga caa ggg att gaa gaa caa aag aat gtc ttg        48
Arg Met Tyr Lys Glu Arg Gln Gly Ile Glu Glu Gln Lys Asn Val Leu
1               5                   10                  15 tca gaa ttt caa aga gat tta aat                                         72
Ser Glu Phe Gln Arg Asp Leu Asn
            20

<210> SEQ ID NO 67
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Met Tyr Lys Glu Arg Gln Gly Ile Glu Glu Gln Lys Asn Val Leu
1               5                   10                  15

Ser Glu Phe Gln Arg Asp Leu Asn
            20
```